(12) United States Patent
Ma et al.

(10) Patent No.: US 9,045,750 B2
(45) Date of Patent: Jun. 2, 2015

(54) HUMANIZED LEWIS-Y SPECIFIC ANTIBODY-BASED DELIVERY OF DICER SUBSTRATE SIRNA (D-SIRNA) AGAINST STAT3

(76) Inventors: Yuelong Ma, Duarte, CA (US); David Horne, Duarte, CA (US); Hua Yu, Duarte, CA (US)

( * ) Notice: Subject to any disclaimer, the term of this patent is extended or adjusted under 35 U.S.C. 154(b) by 0 days.

(21) Appl. No.: 13/424,267

(22) Filed: Mar. 19, 2012

(65) Prior Publication Data
US 2013/0052731 A1 Feb. 28, 2013

Related U.S. Application Data

(60) Provisional application No. 61/454,458, filed on Mar. 18, 2011.

(51) Int. Cl.
| | |
|---|---|
| C07H 21/04 | (2006.01) |
| A61K 39/00 | (2006.01) |
| A61K 39/38 | (2006.01) |
| C12N 15/11 | (2006.01) |
| C07K 1/107 | (2006.01) |
| A61K 47/48 | (2006.01) |
| C12N 15/87 | (2006.01) |
| C12N 15/113 | (2010.01) |

(52) U.S. Cl.
CPC ............ C12N 15/111 (2013.01); C07K 1/1077 (2013.01); A61K 47/48561 (2013.01); C12N 15/87 (2013.01); C12N 15/113 (2013.01); C12N 2310/14 (2013.01); C12N 2310/3513 (2013.01); C12N 2320/32 (2013.01)

(58) Field of Classification Search
CPC ............ C12N 15/113; C12N 2310/14; C12N 2310/3513; C07K 1/1077
See application file for complete search history.

(56) References Cited

U.S. PATENT DOCUMENTS

| | | | |
|---|---|---|---|
| 2006/0030536 A1* | 2/2006 | Yu et al. ............................ 514/44 |
| 2007/0048294 A1* | 3/2007 | Park ............................ 424/93.21 |
| 2009/0202573 A1* | 8/2009 | Zhao et al. .................. 424/179.1 |
| 2010/0226973 A1* | 9/2010 | Fujii et al. ...................... 424/450 |
| 2012/0258104 A1* | 10/2012 | Echeverri et al. .......... 424/134.1 |
| 2013/0035259 A1* | 2/2013 | Schwartz et al. ................ 506/16 |
| 2013/0041140 A1* | 2/2013 | Schwartz et al. .......... 530/391.1 |

OTHER PUBLICATIONS

Solulink, S-SS-4FB, Catalog# S-1037, pp. 1-3, 2013.*
Aigner A: Applications of RNA interference: current state and prospects for siRNAbased strategies in vivo. Appl Micro Biotechno12007, 76: 9-21.
Boghaert ER, Sridharan L, Armellino DC, Khandke KM, DiJoseph JF, Kunz A, Dougher MM, Jiang F, Kalyandrug LB, Hamann PR, Frost P, Damle NK. Antibody-Targeted Chemotherapy with the Calicheamicin Conjugate hu3S193-N-Acetyl γ Calicheamicin Dimethyl Hydrazide Targets Lewisy and Eliminates Lewisy-Positive Human Carcinoma Cells and Xenografts Clinical Cancer Research 2004, 10, 4538-4549.
Daniel MC, Astruc D: Gold nanoparticles: assembly, supramolecular chemistry, quantum-size-related properties, and applications toward biology, catalysis, and nanotechnology. Chern Rev 2004,104: 293-346.
Gingrich JR. Barrios RJ , Morton RA, Boyce BF, DeMayo FJ, Finegold MJ, Angelopoulou R, Rosen JM: Metastatic prostate cancer in a transgenic mouse. Cancer Res, 1996, 56:4096-4102.
Greenberg NM, DeMayo F, Finegold MJ, Medina D, Tilley WD, Aspinall JO, Cunha GR, Donjacour AA, Matusik RJ, Rosen JM: Prostate cancer in a transgenic mouse. Proc Natl Acad Sci USA, 1995, 92:3439-3443.
Kumar S, Harrison N, RichardS-Kortum, R, Sokolov K: Plasmonic nanosencors for imaging intracellular biomarkers in live cells. Nano lett, 2007, 7(5): 1338-1343.
Li I, Yazaki PJ, Anderson AI, Crow D, Colcher D, Wu AM, Williams IE, Wong JYC, Raubitschek A, Shively JE: Improved biodistribution and radioimmunoimaging with poly(ethyleneglycol)-DOTA-conjugated anti-CEA diabody. Bioconjugate Chern, 2006, 17:68-76.
Liu H, Moy P, Xia Y, Kim S, Rajasekaran AK, Navarro V, Knudsen B, Bander NH: Monoclonal antibodies to the extracellular domain of prostate-specific membrane antigen also react with tumor vascular endothelium. Cancer Res, 1997,57:3629-3634.
Matt OM, Nuutinen UM, Hakkarainen T, Tallone T, Wahlfor J, Peikonen J: hCAR-EGFP fusion receptor in human follicular lymphoma B cells—A model for adenoviral gene therapy for B cell malignancies. Int. Mol Med 2006,17: 1057-1062.
Mukherjee P, Bhattacharya R, Bone N, Iee YK, Patra CR, Wang S, Iu I, Secreto C, Banerjee PC, Yaszemski MJ, Kay NE, Mukhopadhyay D: Potential therapeutic application of gold nanoparticles in B-chronic lymphocytic leukemia (BCII): enhancing apoptosis. J Nanobiotechnology 2007, 5:4 doi: 10.1186/1477-3155-5-4.
Nakagawa K, Noguchi Y, Uenaka A, Sato S, Okumura H, Tanaka M, Shimono M, Eldib AMA, Ono T, Ohara N, Yoshino T, Yamashita K, Tsunoda T, Aoe M, Shimizu N, Nakayama E: XAGE-1 expression in non-small cell lung cancer and antibody response in patients. Clin Cancer Res, 2004, 11 (15): 5496.
Paciotti GF, Myer I, Weinreich D, Pavel R, Mclaughlin RE, Tamarkin I: Colloidal gold: a novel nanoparticle vector for tumor directed drug delivery. Drug Deliv 2004, 11 :169-183.

(Continued)

Primary Examiner — Brian Whiteman
(74) Attorney, Agent, or Firm — Perkins Coie LLP; Courtney Prochnow

(57) ABSTRACT

According to some embodiments, methods for covalently or non-covalently conjugating an antibody (e.g., hu3S193 or other humanized antibody) or functional fragment thereof with an siRNA molecule (e.g., anti-STAT3 siRNA) is provided. Such methods may include (1) modifying an antibody or functional fragment thereof with a linker to provide a linker-modified antibody, combining a target siRNA with a disulfide containing aldehyde linker to provide a linker-modified target siRNA and combining the linker-modified target siRNA with linker-modified antibody to form an antibody-siRNA complex; or (2) modifying an antibody or functional fragment thereof with a (Arginine)$_9$ peptide to form an antibody-9R complex and associating an siRNA molecule with the antibody-9R complex to form an electrostatic antibody-9R:siRNA complex. In another embodiment, an antibody-siRNA conjugate may be used in methods for suppressing or silencing STAT3 protein expression in a cancer cell.

11 Claims, 55 Drawing Sheets

(56) References Cited

OTHER PUBLICATIONS

Qu ZX, Goldenberg OM, Cardillo TM, Shi V, Hansen HJ, Chang CH: Bispecific antiCD20/22 antibodies inhibit B-cell lymphoma proliferation by a unique mechamism of action. Blood, 2007: DOI10.11821blood-2007-08-110072.

Rosi NI, Giljhann DA, Thazton CS, Iytton-Jean, AKR, Han MS, Mirkin CA: Oligonucleotide-modified gold nanoparticles for intracellular gene regulation. Science, 2006,312: 1027-1030.

Scott AM, Tebbutt N, Lee FT, Cavicchiolo T, Liu Z, Gill S, Poon A, Hopkins W, Smyth FE, Murone C, MacGregor O, Papenfuss A, Chappell B, Saunder T, Johns TG, Brechbiel MW, Davis 10, Murphy R, Chong G, Stockert E, Ritter G, Hoffman EW, Old IJ: Phase I trial of humanized monoclonal antibody hu3S193 in patients with advance epithelial cancers which express the lewis-y antigen. Clin Cancer Res, 2007, 13(11):3286-3292.

Silver DA, Pellicer I, Fair WR, Heston WDW, Cordon-Cardo C: Prostate-specific membrane antigen expression in normal and malignant human tissues. Clin Cancer Res, 1997, 3:81-85.

Simpson AJG, Caballero OL, Jungbluth A, Chen YT, Old IJ: Cancer/testis antigens, gametogenesis and cancer. Nature Reviews Cancer, 2005, 5, 615-625.

Smith MR: Rituximab (monoclonal anti-CD20 antibody): mechanism of action and resistance. Oncogene 2003,22: 7359-7368.

Wang T, Niu G, Kortylewski M, Jove R, Yu H: Regulation of the innate and adaptive immune responses by 51al-3 signaling in tumor cells. Nature Medicine, 2004, 10:48• 54.

Yu H, Jove R: The STATs of cancer—new molecular targets come of age. Nature Rev Cancer, 2004,4:97-105.

Yu H, Kortylewski M, Pardoll D: Crosstalk between cancer and immune cells: Role of STAT3 in tumour microenvironment. Nature Rev Immunology, 2007, 7:41-51.

* cited by examiner

Sense Strands with unmodified 5'-terminus

S1  5'-rGrGrA rArGrC rUrGrC rArGrA rArArG rArUrA rCrGrA rCrUdG dA-3'
S2  5'-rGrGrA rArGrC rUrGrC rArGrA rArArG rArUrA rCrGrA rCrUrG rA-3'
S3  5'-rGrGrA rArGfC fUrGfC rArGrA rArArG rAfUrA fCrGrA fCfUdG dA-3'

AntiSense Strand with unmodified 5'-terminus

A1  5'-rUrCrA rGrUrC rGrUrA rUrCrU rUrUrC rUrGrC rArGrC rUrUrC rCrGrU-3'

2'-Fluoro Uridine (fU)

Sense Strands with Modified 5'-terminus

S1-NH₂  H₂N-(CH₂)₆-O-P(O⁻)(=O)-O-(CH₂)₃-O-P(O⁻)(=O)-O -rGrGrA rArGrC rUrGrC rArGrA rArArG rArUrA rCrGrA rCrUdG dA-3'

S2-NH₂  H₂N-(CH₂)₆-O-P(O⁻)(=O)-O-(CH₂)₃-O-P(O⁻)(=O)-O -rGrGrA rArGrC rUrGrC rArGrA rArArG rArUrA rCrGrA rCrUrG rA-3'

S3-NH₂  H₂N-(CH₂)₆-O-P(O⁻)(=O)-O-(CH₂)₃-O-P(O⁻)(=O)-O -rGrGrA rArGfC fUrGfC rArGrA rArArG rAfUrA fCrGrA fCfUdG dA-3'

AntiSense Strand with Modified 5'-terminus

A1-NH₂  H₂N-(CH₂)₆-O-P(O⁻)(=O)-O-(CH₂)₃-O-P(O⁻)(=O)-O -rUrCrA rGrUrC rGrUrA rUrCrU rUrUrC rUrGrC rArGrC rUrUrC rCrGrU-3'

Figure 9

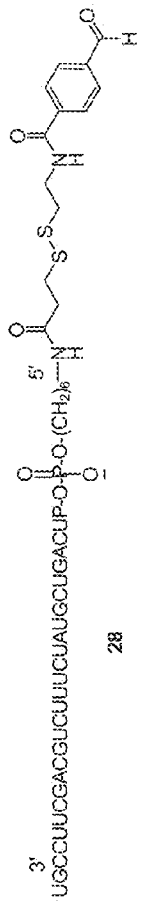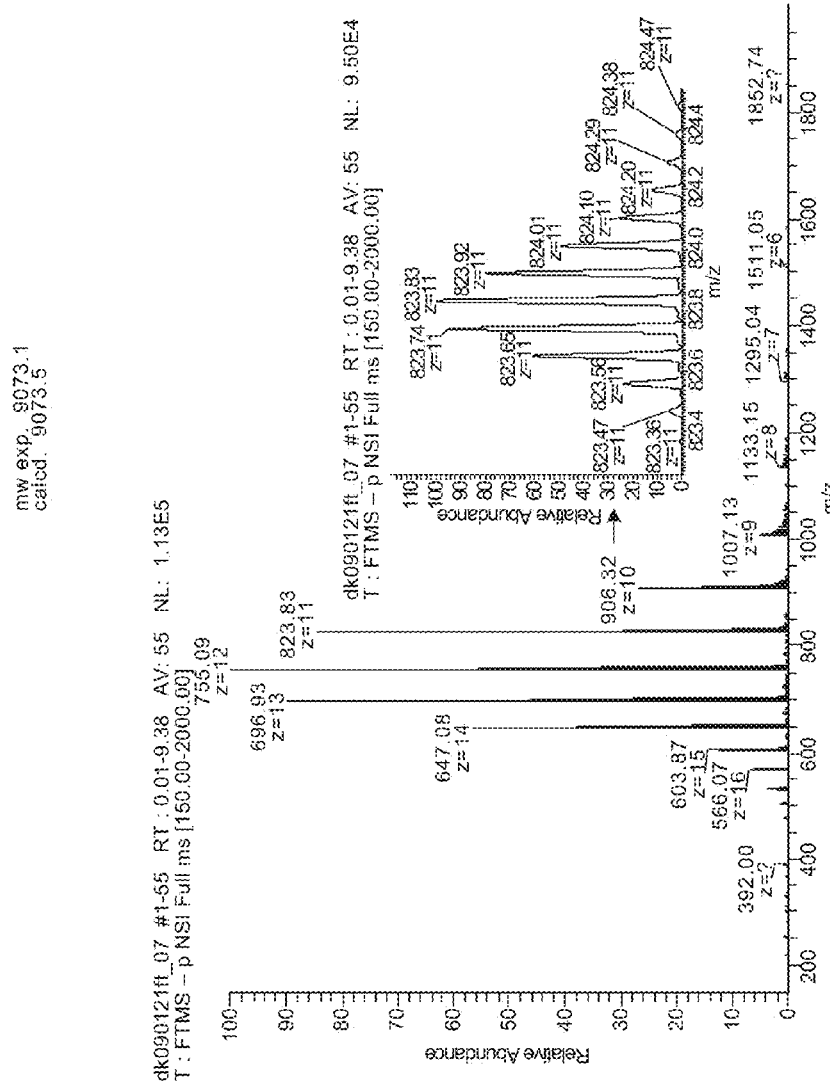
FIG. 12

- duplicate experiments using a PE conjugated secondary antibody

HUMANIZED LEWIS-Y SPECIFIC ANTIBODY-BASED DELIVERY OF DICER SUBSTRATE SIRNA (D-SIRNA) AGAINST STAT3

CROSS REFERENCE TO RELATED APPLICATIONS

This application claims the benefit of U.S. Provisional Patent Application No. 61/454,458, filed Mar. 18, 2011, which is hereby incorporated by reference in its entirety.

BACKGROUND

RNA interference (RNAi) is a technique in which exogenous, double-stranded RNAs (dsRNAs) are introduced into a cell to specifically destroy a particular mRNA or block its expression, thereby diminishing or abolishing gene expression. Specific types of RNAs, such as small interfering RNAs (siRNAs) and micro interfering RNAs (miRNAs) have been shown to inhibit expression of a number of specific genes effectively and the technique has proven effective in various cell cultures, including mammalian cell cultures. Because small interfering RNA molecules are directed to a specific target and thereby silence a specific gene, they have been suggested to be useful in treatment of diseases as well as for screening new pharmaceuticals and disease mechanisms for pharmaceutical target determination. However, delivery of RNA interfering agents, including siRNAs and miRNAs, into cells has proven to be challenging.

Various methods to deliver RNA interference molecules into cells are known, and include chemical transfection using lipid-based, amine-based and polymer-based techniques, and combinations thereof. Unfortunately, efficient transfer of RNA interfering agents, including siRNAs into primary cells by chemical transfection seems to be restricted to a few cell types. Other ways to deliver siRNAs include expressing short hairpin RNA molecules from vectors include lentiviral constructs, and introducing siRNA molecules into cells using electroporation. However, these methods are also have shortcomings. Viral delivery has issues related to permanent integration and electroporation is a harsh treatment that cannot generally be used to deliver siRNAs into cells in vivo. Further, these RNA interference delivery methods target all cells non-specifically.

Therefore, it would be useful to develop RNAi delivery methods that target specific cells, thereby minimizing or avoiding potential side effects caused by delivery of RNA interference into non-target cells.

SUMMARY

In one embodiment, a method for covalently conjugating an antibody or functional fragment thereof with an siRNA molecule is provided. Such a method includes modifying an antibody or functional fragment thereof with a linker to provide a linker-modified antibody, combining a target siRNA with a disulfide containing an aldehyde linker to provide a linker-modified target siRNA and combining the linker-modified target siRNA with the linker-modified antibody to form an antibody-siRNA complex. In some aspects the antibody is a humanized antibody such as hu3S193 and the siRNA molecule is an siRNA against STAT3.

In some aspects, the linker-modified antibody is modified with a 6-hydrazin onicotinamide (HyNic) linker and the disulfide containing aldehyde linker is a succinimidyl-4-formyl benzoate analog that includes a disulfide bond (S-SS-4FB). Alternatively, the disulfide containing aldehyde linker is phosphoramidite.

In another embodiment, a method for non-covalently conjugating an antibody or functional fragment thereof with an siRNA molecule is provided. Such a method includes modifying an antibody or functional fragment thereof with a (Arginine)$_9$ peptide to form an antibody-9R complex and associating an siRNA molecule with the antibody-9R complex to form an electrostatic antibody-9R:siRNA complex. In some aspects the antibody is a humanized antibody such as hu3S193 and the siRNA molecule is an siRNA against STAT3.

In another embodiment, a method for suppressing or silencing STAT3 protein expression in a cancer cell is provided. Such a method includes administering to a Lewis Y antigen ($Le^Y$) positive cell, an effective amount of an antibody-siRNA conjugate comprising a Lewis Y ($Le^Y$) antibody conjugated to an siRNA against STAT3. In some aspects, the antibody is a hu3S193 antibody.

In some aspects, the $Le^Y$ antibody may be conjugated to the siRNA by covalent conjugation or by non-covalent conjugation according to the embodiments described above. In other aspects, an endosome escape reagent such as chloroquine (CQ) or (Arginine)$_9$ may also be administered when covalent conjugation is used.

BRIEF DESCRIPTION OF THE DRAWINGS

FIG. 9 shows the following substrates for an siRNA duplex according to some embodiments: sense strands with unmodified 5'-terminus (S1-S3)(SEQ ID NOS: 1-3), an antisense strand with unmodified 5'-terminus (A1)(SEQ ID NO: 4), sense strands with modified 5'-terminus (S1-NH$_2$, S2-NH$_2$ and S3-NH$_2$)(SEQ ID NOS: 5-7) and an antisense strand with modified 5'-terminus (A1-NH$_2$)(SEQ ID NO: 8).

FIG. 12 (SEQ ID NO: 8) is an LTQ-FT mass spectrum confirming the identity of linker-modified siRNA 28.

DETAILED DESCRIPTION

Antibody-siRNA conjugates, methods of synthesizing antibody-siRNA conjugates and methods for their use are provided herein. Such methods may be used to synthesize antibody-siRNA conjugates having any combination of mAbs and siRNAs. In some embodiments, the antibody-siRNA conjugates specifically target Le$^Y$ antigen expressing cancer cells to deliver an siRNA molecule that suppresses signal transducer and activator of transcription 3 (STAT3) expression.

The antibody-siRNA conjugates (or "complexes") include an antibody or functional fragment thereof that targets a cancer cell to selectively deliver an associated siRNA molecule to the cell. An antibody or functional antibody fragment is a molecule that includes one or more portions of an immunoglobulin or immunoglobulin-related molecule that specifically binds to, or is immunologically reactive with a cancer-related antigen or other cancer biomarker. The antibody may be a polyclonal antibody, a monoclonal antibody, or any suitable modified antibody. The term modified antibody includes, but is not limited to genetically engineered or otherwise modified forms of immunoglobulins, such as intrabodies, chimeric antibodies, fully human antibodies, humanized antibodies, and heteroconjugate antibodies (e.g., bispecific antibodies, diabodies, triabodies, and tetrabodies). The term functional antibody fragment includes one or more antigen binding fragments of an antibody alone or in combination with other molecules, including, but not limited to Fab', F(ab')$_2$, Fab, Fv, rIgG, scFv fragments, single domain fragments, peptibodies, minibodies and cys-diabodies. The term scFv refers to a single chain Fv antibody in which the variable domains of the heavy chain and of the light chain of a traditional two chain antibody have been joined to form one chain. The term "antibody" as used herein may refer to an antibody, monoclonal antibody, modified antibody or any functional fragments thereof.

In one embodiment, the antibody or functional fragment thereof is a monoclonal antibody or functional fragment thereof. Monoclonal antibodies (mAbs) provide a higher specificity for delivery of siRNA payloads to tumor cells than polyclonal antibodies. The monoclonal antibody or functional fragment thereof may target any cancer or tumor associated antigen or receptor associated with, expressed or over-expressed by the surface of a cancer cell, for example, Lewis Y (Le$^Y$) antigen, prostate specific membrane antigen (PSMA), cancer/testis antigens (e.g., XAGE-1) alphafetoprotein (AFP), Carcinoembryonic antigen (CEA) or any other suitable antigen or receptor that is expressed or overexpressed by cancer cells.

Figure 27:
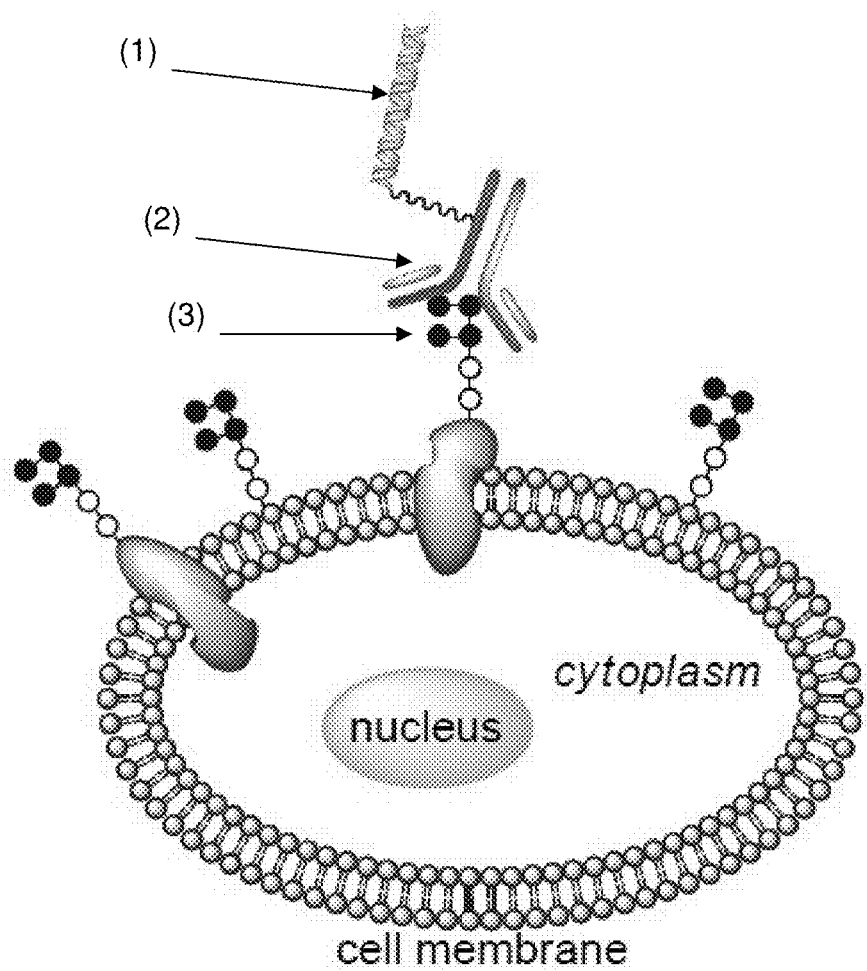
FIG. 27 is a schematic diagram of an antibody-siRNA delivery vehicle according to one embodiment. A dicer substrate siRNA (D-siRNA) against STAT3 (1) is conjugated to an hu3s193 antibody (2) that recognizes a Lewis Y ($Le^Y$) antigen (3) at the cell surface.
Figure 28A:
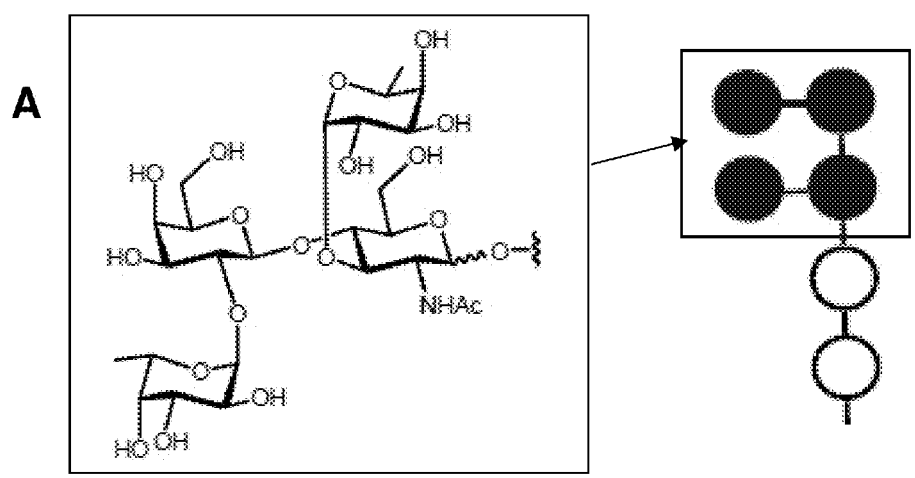
FIG. 28 illustrates the $Le^Y$ antigen. $Le^Y$ is a type 2 blood group-related difucosuylated oligosaccharide that occurs at the plasma membrane as a glycolipid or linked to surface receptors (e.g., ErbB family). (A) Shows the core structure of $Le^Y$ and a representative schematic diagram representing the core structure. The core structure is linked to the plasma membrane via a glycolipid or a surface receptor (B).
Figure 28B:
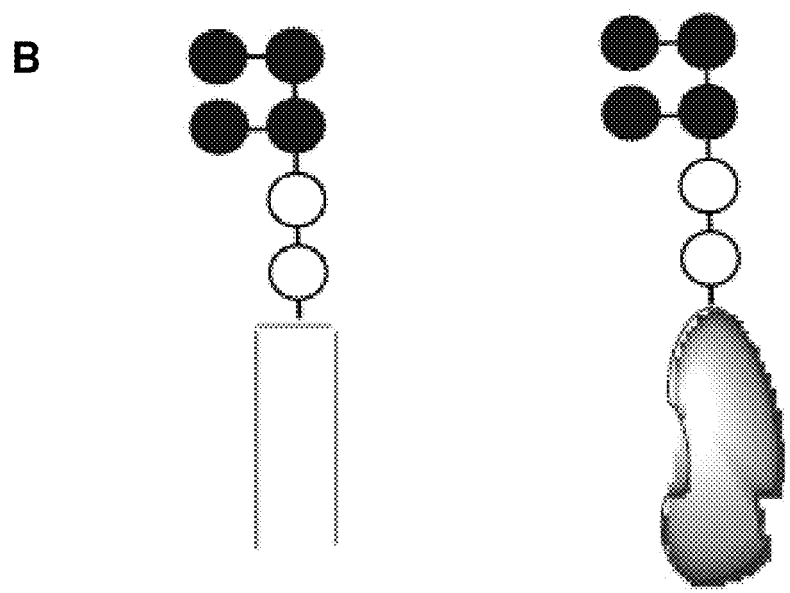

In one embodiment, the monoclonal antibody or functional fragment thereof may target the Lewis Y antigen. The Le$^Y$ antigen is a blood group-related antigen expressed in over 70% of epithelial cancers including breast, colon, ovary, pancreatic, prostate and lung cancers. The structure of the Le$^Y$ antigen is shown in FIG. 28(A). The Le$^Y$ antigen is linked to a glycolipid or a surface receptor found on the plasma membrane of Le$^Y$ antigen positive (Le$^{Y+}$) cancer cells (FIG. 28B). When a monoclonal antibody or functional fragment thereof binds a Le$^Y$ antigen associated with a surface receptor (FIG. 27), the monoclonal antibody or functional fragment, along with any molecule attached thereto, may be internalized in a receptor-mediated endocytosis process. Therefore, when the monoclonal antibody or functional fragment thereof is conjugated to an siRNA molecule as described below, the internalized antibody-siRNA conjugate allows for intracellular delivery of the siRNA into the target cell.

Figure 29:
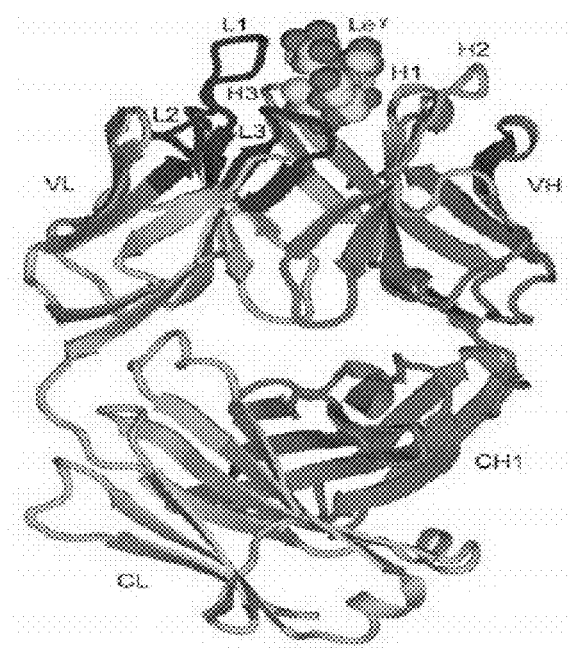
FIG. 29 shows the crystal structure of the hu3S193 Fab complex with $Le^Y$. The humanized $Le^Y$ antibody hu3S193 binds specifically with $Le^Y$ antigen. The hu3S193 antibody is well tolerated and selectively targets $Le^Y$-expressing tumors. After antigen recognition, the $Le^Y$-hu3S193 complex can be internalized by the cell. The hu3S193-calicheamicin conjugate selectively inhibits $Le^Y$ tumor growth.

In one embodiment, the monoclonal antibody or functional fragment is a humanized hu3S193 monoclonal antibody (FIG. 29). The hu3S193 antibody against Le$^Y$ ("hu3S193" or "mAb$_{hU3s193}$") is well tolerated by subjects and selectively targets Le$^Y$-expressing tumors (Scott et al. 2007).

The antibody-siRNA conjugate also includes an siRNA molecule that is designed to target and suppress or block the expression of a gene or protein associated with cancer or is involved in the development and/or progression of cancer. Treatment using siRNA molecules offers many potential advantages over small-molecule drugs such as the ability to design a specific siRNA compound for any target gene of interest within short periods of time and at comparatively low development costs.

In one embodiment, the siRNA is an siRNA against STAT3 ("siRNA$_{STAT3}$" or "siSTAT3"), i.e., the siRNA suppresses the expression of STAT3. The STAT family of proteins is a group of transcription factors that regulate many aspects of growth, survival and differentiation in cells. One STAT family member, STAT3, is persistently activated in a wide diversity of solid tumors and blood malignancies. Moreover, STAT3 has an important role in malignant progression by subversion of fundamental biological processes. Specifically, activated STAT3 enhances tumor cell proliferation and survival, in part by inducing expression of cell cycle control genes and anti-apoptosis genes. Furthermore, it has been demonstrated that activated STAT3 stimulates tumor angiogenesis and suppresses antitumor immune responses in the tumor microenvironment. Thus, persistent STAT3 activation contributes to both tumor-cell intrinsic and extrinsic mechanisms of malignancy, making it an excellent target for cancer therapy. For example, a panel of computationally designed Dicer substrate 27-mer siRNAs (D-siRNA) against STAT3 has been screened and several STAT3 siRNA candidates have been shown to inhibit STAT3 expression in vitro.

In another embodiment, additional conjugates in which the mAb and/or the siRNAs selectively target Cancer/Testis (CT) antigens may be developed. CT antigens are expressed in various types of cancer and male germ cells in the testis but not in adult somatic tissues. CT antigens have been implicated as tumorigenic through their individual or coordinated expression in non-transformed cell lines (Simpson et al. 2005). CT antigens, such as XAGE-1, may serve as susceptible targets to a range of treatment modalities beyond cancer vaccines. For instance, non-small cell lung cancer has high levels of expression of XAGE-1b, which also is immunogenic (Nakagawa et al. 2004). Thus, a mAb$_{XAGE-1}$-siRNA$_{XAGE-1}$ conjugate may be used to further understand role of CT antigens in tumorigenesis.

Either component of the antibody-siRNA conjugate complex, the siRNA molecule or the antibody, may be labeled or modified by a visualization agent. A "visualization agent" is an atom, molecule, or compound that is useful in diagnosing, detecting or visualizing the antibody-siRNA conjugate in a cell by in vivo or in vitro methods. According to the embodiments described herein, diagnostic agents may include, but are not limited to, radioactive substances (e.g., radioisotopes, radionuclides, radiolabels or radiotracers), dyes, contrast agents, fluorescent compounds (e.g. FAM) or molecules, bioluminescent compounds or molecules, enzymes and enhancing agents (e.g., paramagnetic ions).

According to some embodiments, one or more antibodies, one or more siRNAs, one or more antibody-siRNA conjugates or a combination thereof may be further conjugated to a nanoparticle, such as a gold nanoparticle (AuNP). A single AuNP can contain a relatively large amount of drug molecules, thereby producing a high local drug concentration when delivered to a subject. When coupled to a target-specific antibody, a highly specific therapeutic agent is created.

Colloidal AuNPs was first reported by Michael Faraday in 1857. The use of gold as the particle platform has several advantages over other nanoparticle-based materials. First, Au is a relatively inert element, possessing minimal toxicity compared to other materials. Studies in the 1950s and 60s showed that intravenous administration of radioactive colloidal gold nanoparticles based on Au$^{198}$ for the treatment of liver cancer and sarcoma resulted in drug-associated toxicities due to radiation exposure, not due to the particles themselves (Paciotti et al. 2004). Recent reports have also confirmed biocompatability of non-radioactive AuNPs (Daniel & Astruc 2004; Paciotti et al. 2004; Mukherjee et al. 2007). The absence of particle toxicity makes gold a viable choice for in vivo applications. Second, AuNPs can be produced with very high precision and controlled dimensions of varying nano-sized spheres so that their characterization is relatively straightforward. Third, Au can be easily functionalized with thiol-based reagents, thereby allowing these nanoparticles to be associated with a number of biological and small molecule appendages for various applications.

In one embodiment, the mAbs, siRNAs and antibody-siRNA conjugates or a combination thereof are conjugated to gold nanoparticles (AuNPs) for the development of selective therapies for the treatment of cancers. Chemical methods for the construction of heterofuntional AuNPs possessing at least two functionally distinct biomolecules (i.e. AuNP-Anti-body$_1$-Antibody$_2$ and AuNP-antibody-siRNA conjugates) in a highly controlled manner may be developed. These methods should result in the production of effective therapeutic compositions that have low toxicity to the subject.

Methods for Constructing Antibody-siRNA Conjugates

Figure 30:
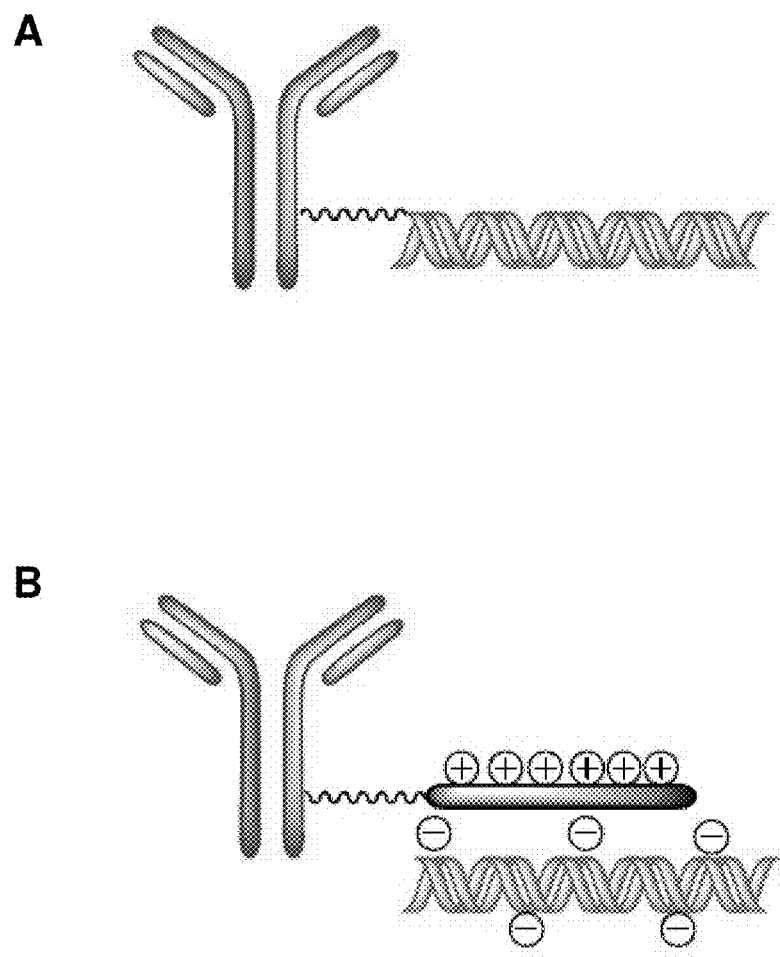
FIG. 30 are schematic diagrams illustrating a covalent strategy for constructing antibody-based siRNA delivery vehicles (A) and a non-covalent strategy for constructing antibody-based siRNA delivery vehicles (B) according to embodiments described herein.

The antibody-siRNA conjugates or complexes may be synthesized or constructed using any suitable conjugation method. In one embodiment, the antibody-siRNA complex is constructed by a method of covalent conjugation. Synthesis of antibody-siRNA conjugates via a covalent construction strategy involves chemically linking an siRNA molecule to an antibody using a cleavable or non-cleavable linker (FIG. 30A).

Figure 1:
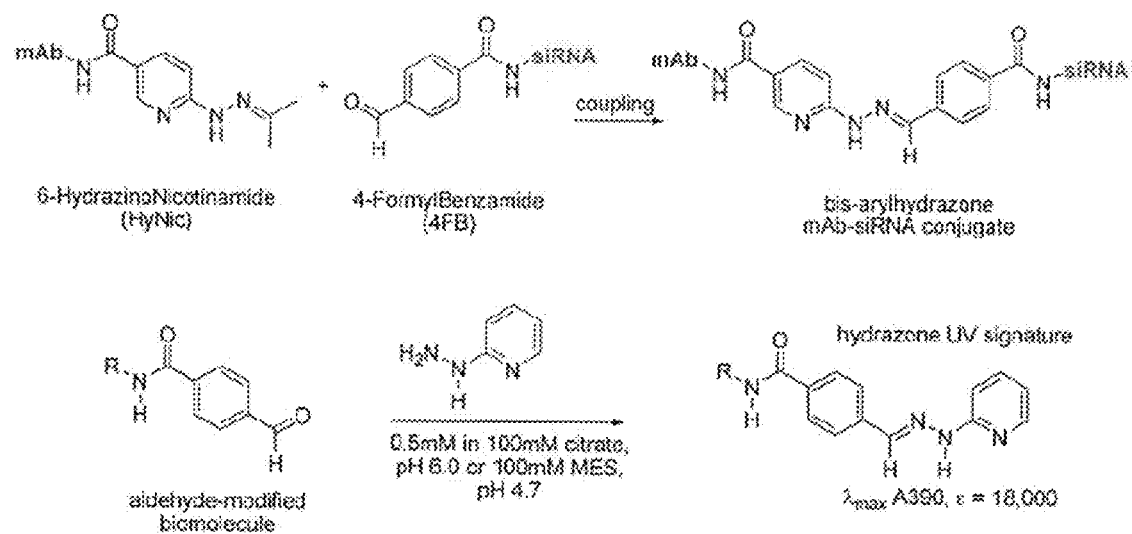
FIG. 1 is a schematic diagram illustrating the chemical equations associated with conjugation of mAbs and siRNAs via HyNic and 4FB linkers according to one embodiment.
Figure 2:
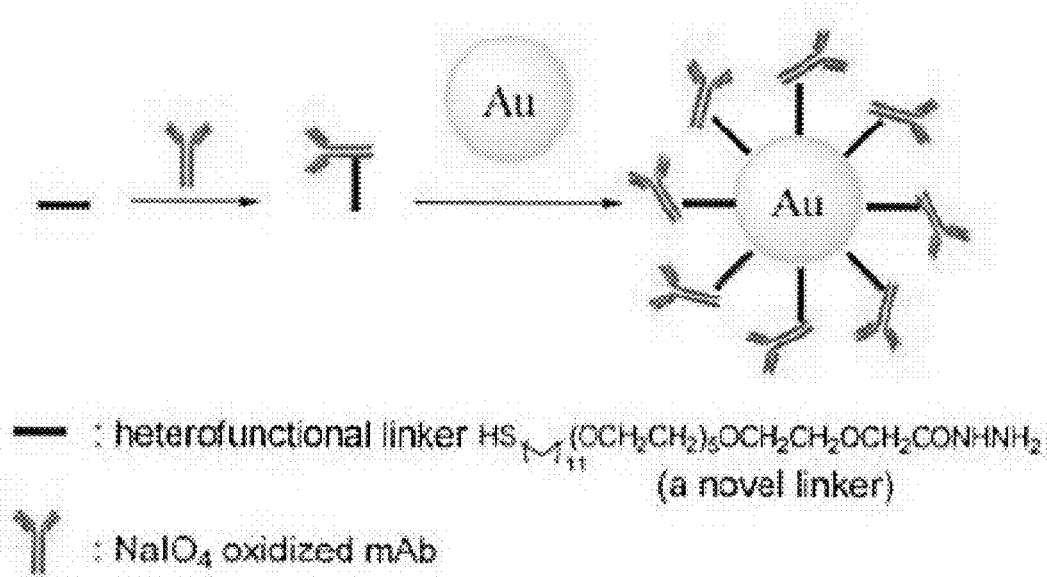
FIG. 2 is a schematic diagram illustrating the generalized construction of an AuNP-mAb conjugate.
Figure 3:
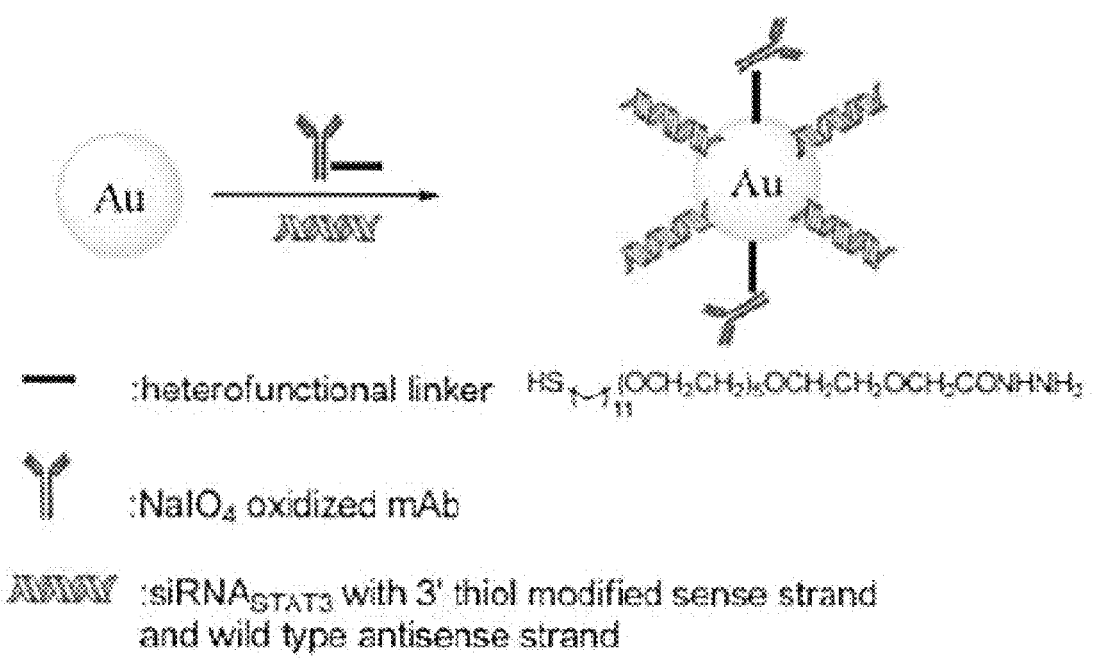
FIG. 3 is a schematic diagram illustrating the generalized construction of an AuNP-mAb-siRNA$_{STAT3}$ conjugate.
Figure 4:
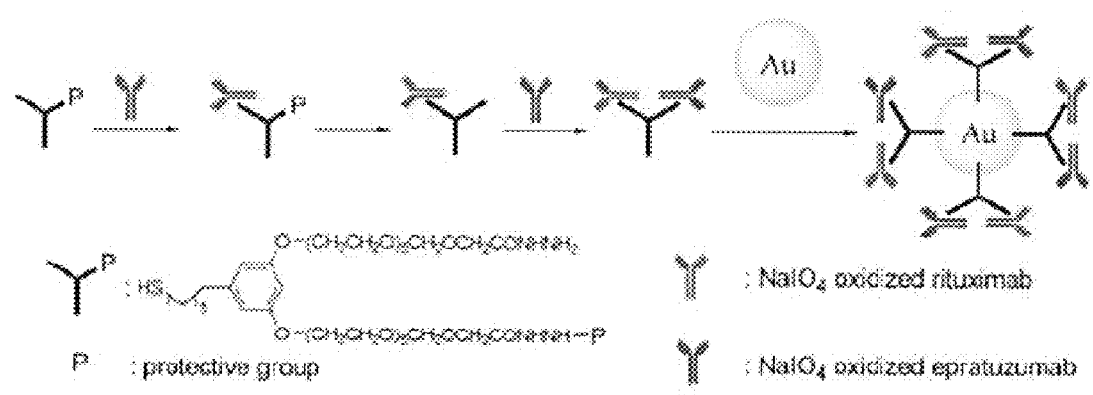
FIG. 4 is a schematic diagram illustrating the generalized construction of a synthetic hyper-crosslinked mAb$_1$ and mAb$_2$ conjugated AuNP.

The method of covalent conjugation may include a step of modifying an antibody or functional fragment thereof with a linker to provide a linker-modified antibody and a step of combining a target siRNA with a disulfide containing aldehyde linker to provide a linker-modified target siRNA. In some embodiments, the bioconjugation chemistry used to perform the linker modifications are based on two heterobifunctional linkers, a 6-hydrazin onicotinamide (HyNic) to modify the antibody and a 4-formylbenzamide (4FB) or 4FB analog to modify the siRNA (Solulink). HyNic and 4FB are designed to be complementary in nature and to react only with each other (FIG. 1). Both HyNic and 4FB attach to amino groups of the respective biomolecules via N-hydroxysuccinamide chemistry.

The method of covalent conjugation also includes a step of combining the linker-modified target siRNA with linker-modified antibody to form an antibody-siRNA complex or conjugate. Briefly, once HyNic and 4FB are attached to the mAb and siRNA, respectively, they can be combined to form the desired mAb-siRNA conjugate via a stable hydrazone covalent linkage (FIG. 1). The arylhydrazone mAb siRNA conjugate has a characteristic UV absorbance signature that can be easily monitored to assess efficiency of the coupling reaction.

Figure 5:
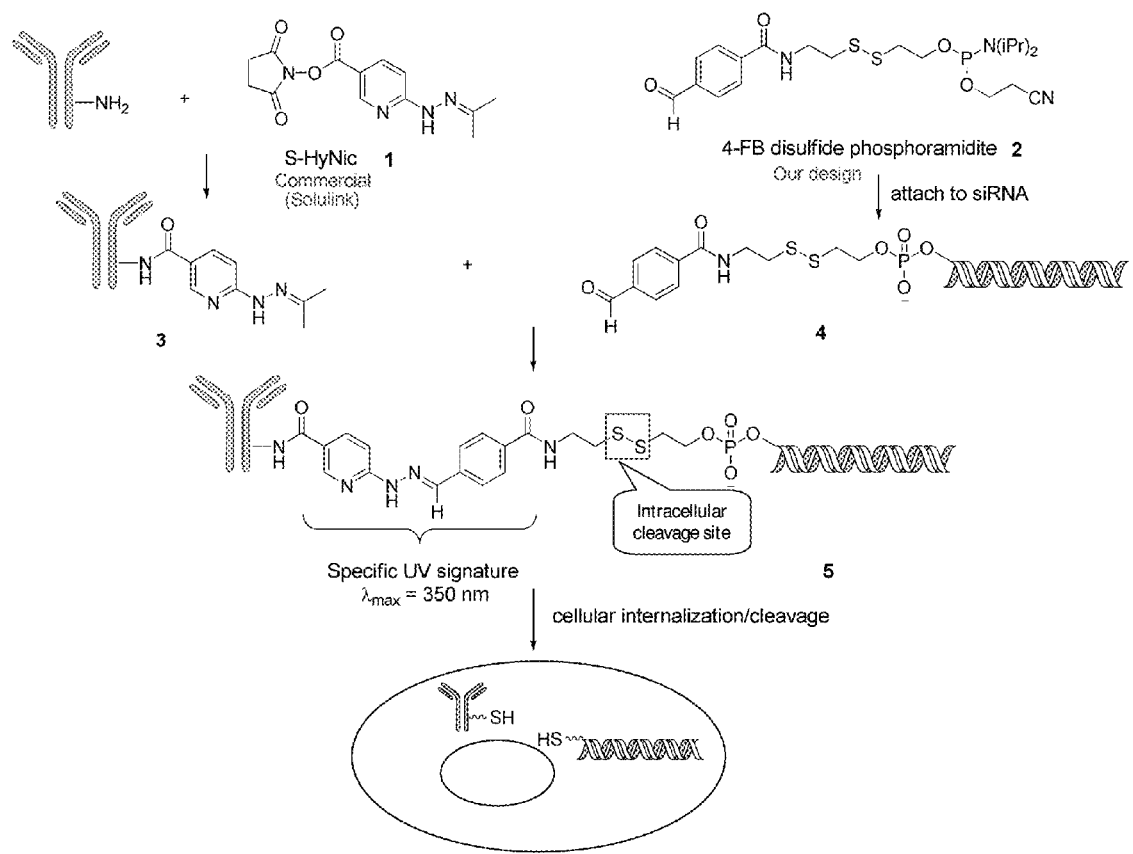
FIG. 5 is a schematic diagram illustrating the chemical equations that are associated with the construction of an hu3S193 antibody-siRNA conjugate according to some embodiments.

In one embodiment, the method of covalent conjugation is illustrated in FIG. 5. Briefly, a humanized antibody, hu3S193, may be modified with a HyNic linker (Solulink) 1 to produce an activated, or linker-modified, antibody 3. In turn, 3 will be conjugated or combined with a linker-modified siRNA derivatized aldehyde 4 to produce the desired antibody-siRNA conjugate or complex 5, which has a disulfide intracellular cleavage site (e.g. mAb$_{hu3S193}$-siRNA$_{STAT3}$ or hu3S193-siSTAT3). The linker-modified siRNA 4 is synthesized by modifying the siRNA with phosphoramidite 2.

In some aspects, phosphoramidite 2 is a moiety that may be used to link the siRNA and antibody. It is a tri-functional molecule that contains a phosphoramidite for solid phase RNA synthesis, a cleavable disulfide bond for release after cellular internalization, and a benzaldehyde unit for conjugation to the antibody via a stable hydrazone bond. The penultimate intermediate 14 has been prepared and structurally characterized. A series of disulfide exchange reactions were utilized in the preparation of this intermediate. After obtaining compound 14 it may be transformed to phosphoramidite. 2.

Figure 7:
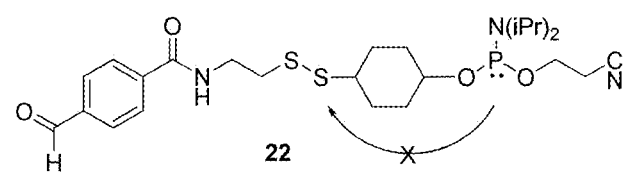
FIG. 7 is a schematic diagram illustrating a solution for improved synthesis of phosphoramidite 2 according to some embodiments.

In addition, success in transforming the intermediate to phosphoramidite 2 may be improved by increasing the length of carbon chain between disulfide and phosphoramidite and/or introducing a structural constraint by an intervening ring motif to prevent the phosphorus center from cleaving the disulfide unit (see compound 22, FIG. 7).

Figure 8:
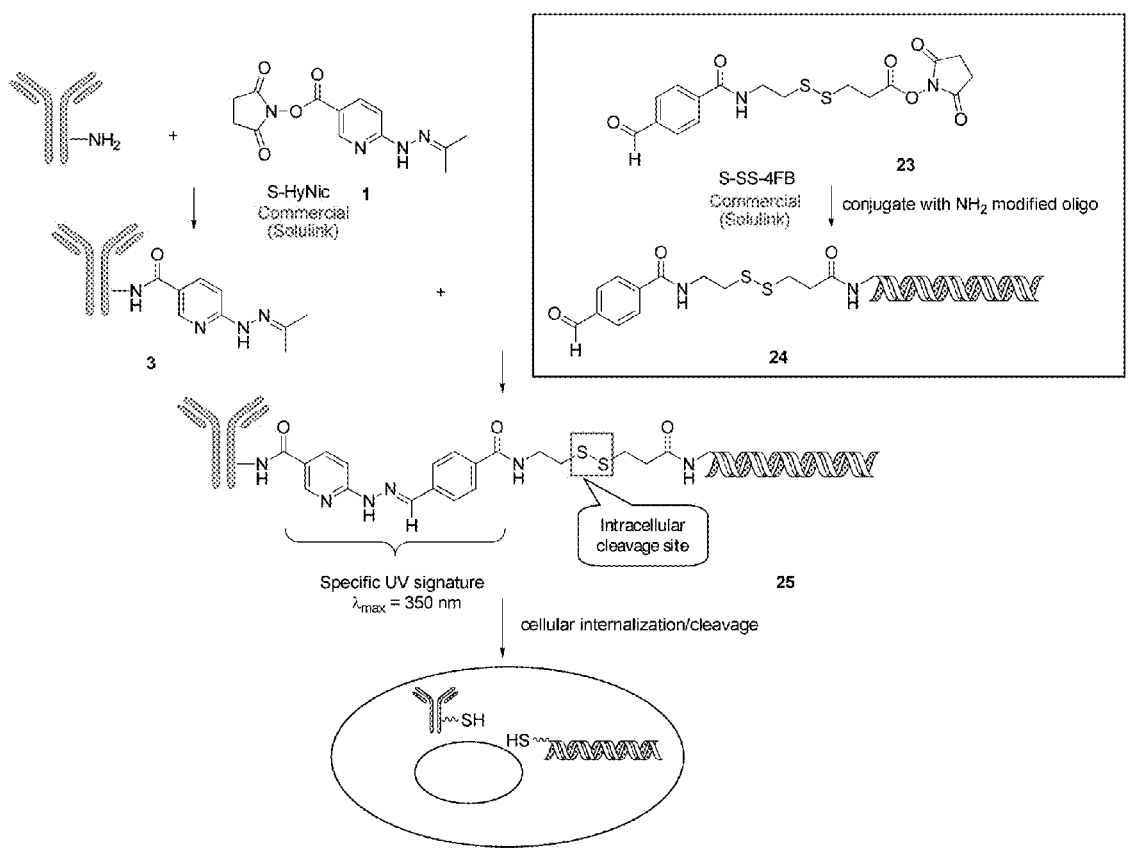
FIG. 8 is a schematic diagram illustrating the chemical equations associated with the construction of an hu3S193 antibody-SS-aldehyde-siRNA construct according to some embodiments.

In another embodiment, the method of covalent conjugation is illustrated in FIG. 8. In this embodiment, a post-synthetic modification was performed instead of the direct solid-phase synthesis described above. Briefly, the 5'-end amino modified single strand was synthesized via solid-phase synthesis. Then the single stranded RNA reacts with a disulfide containing aldehyde linker 23 (S-SS-4FB; Solulink) to provide a linker-modified single stranded substrate, which, when annealed with its RNA complement affords the fully loaded siRNA duplex 24. Coupling of 3 and 24 produces the desired hu3S193-siRNA conjugate 25 which could be analyzed as previously described.

The methods described above provide an expeditious method for synthesizing antibody-siRNA conjugates and allows the siRNA component to be released from the conjugate upon internalization via a disulfide intracellular cleavage site. In addition, as described in the Examples below, a non-cleavable siRNA conjugate may be constructed to study the effects of "free" vs. "antibody-conjugated" siRNA systems. The non-cleavable construct has two methylene (carbon) units that replace the disulfide moiety. Upon processing of free siRNA by dicer and RISC, gene silencing should occur.

Further, when conjugated to an siRNA using the methods described herein, the immunoreactivity of the antibodies is not adversely affected. For example, in a previous study, the humanized anti-Le$^Y$ hu3S193 antibody was conjugated to the small DNA cleaving molecule, calicheamicin (Boghaert et al. 2004). Although the calicheamicin study does not use the same activated ester substrate or payload as provided herein, the conjugation of the antibody using activated ester methodology did not adversely affect the immunoreactivity of the resulting antibody-calicheamicin conjugate.

In another embodiment, the antibody-siRNA complex is constructed by a method of non-covalent conjugation. Synthesis of antibody-siRNA conjugates via a non-covalent construction strategy involves modification of an antibody or functional fragment thereof with positively charged vehicles (e.g. peptides and polymers) which electrostatically interact with negatively charged siRNA (FIG. 30B). Therefore, according to some embodiments, the method of non-covalent conjugation may include a step of modifying an antibody or functional fragment thereof with a positively charged peptide to form an antibody-peptide complex. In one embodiment, the antibody or functional fragment thereof is modified with a peptide having nine Arginine residues ("(Arg)$_9$," "(Arginine)$_9$," or "9R") to form an antibody-9R complex. The antibody-9R complex may be a humanized antibody, such as a hu3S193 antibody modified with a 9R peptide to form a hu3S193-9R complex.

The method of non-covalent conjugation may also include a step of associating an siRNA molecule with the antibody-9R complex to form an electrostatic antibody-9R:siRNA complex. In some embodiments, the siRNA molecule is an siRNA against STATS that is associated with a hu3S193-9R complex to form a hu3S193-9R:siSTAT3 complex.

Treatments for Cancer

The antibody-siRNA conjugates described herein may be used in methods to treat a variety of cancers, to attenuate the growth of a tumor or to prevent metastasis of a tumor. Such methods may be used to treat or attenuate the growth of any cancer or tumor type. Cancers and tumor types that may be treated or attenuated using the methods described herein include but are not limited to bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma and leukemia, melanoma, ovarian cancer, pancreatic cancer, pituitary cancer, prostate cancer, rectal cancer, renal cancer, sarcoma, testicular cancer, thyroid cancer, and uterine cancer. In addition, the methods may be used to, treat tumors that are malignant (e.g., primary or metastatic cancers) or benign (e.g., hyperplasia, cyst, pseudocyst, hematoma, and benign neoplasm).

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The antibody-siRNA conjugates described herein may be part of a therapeutic composition that may also include one or more pharmaceutically acceptable carrier. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The cancer may be treated by using a method for suppressing or silencing the expression of a gene or protein in a cancer cell, which may lead to suppressing proliferation of the cancer cell. Such a method may include administering an effective amount of an antibody-siRNA conjugate to a cancer cell. In one embodiment, a method for suppressing or silencing STAT3 protein expression in a cancer cell is provided. The method includes administering to a Le$^{Y+}$ cell an effective amount of a Le$^Y$ antibody (e.g. hu3S193) conjugated to an siRNA against STAT3 (e.g., an hu3S193-siSTAT complex or a hu3S193-9R:siSTAT3 complex or conjugate as described above). Such methods that result in suppressing or silencing STAT3 protein expression in a cancer cell may, as a result, suppress proliferation of the cancer cell, thereby attenuating tumor growth and/or cancer progression.

An "effective amount," "therapeutically effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005

In one embodiment, the Le$^Y$ antibody is conjugated to the siRNA by covalent conjugation. The covalent conjugation may be accomplished by modifying the Le$^Y$ antibody with a linker to provide a linker-modified Le$^Y$ antibody, combining the siRNA (e.g., siSTAT3) with a disulfide containing aldehyde linker to provide a linker0modified STAT3 siRNA, and combining the linker-modified siRNA with the linker-modified Le$^Y$ antibody to form a Le$^Y$ antibody-siRNA complex (e.g., a hu3S193-siSTAT complex or conjugate). When covalent conjugation is used, the method for silencing STAT3 protein expression in a cancer cell further includes administering an effective dose of an endosome escape reagent. The endosome escape reagent may be, for example, chloroquine (CQ) or 9R.

In another embodiment, the Le$^Y$ antibody is conjugated to the siRNA by non-covalent conjugation. The non-covalent conjugation may be accomplished by modifying the Le$^Y$ antibody with an (Arginine)$_9$ (9R) peptide to form a Le$^Y$ antibody-9R complex; and electrostatically associating the siRNA molecule with the Le$^Y$ antibody-9R complex to form an antibody-9R:siRNA complex (e.g., a hu3S193-9R:siSTAT3 complex or conjugate).

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The Examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLE 1

Generation of Covalently Conjugated Monoclonal Antibodies and siRNAs

Construction of Linker-modified Target siRNA

Using the approach described above and illustrated in FIG. 8, a number of sense and antisense siRNA strands were prepared and summarized in FIG. 9. For the three sense strands with an unmodified 5'-terminus, S1 has two DNA base pairs (bp) at 3' end, S2 has no modifications, S3 has two DNA by at the 3' end plus fluorine substitution at 2'-position in ribose as illustrated. The two DNA by is thought to increase the gene knockdown efficiency of the dicer-substrate siRNA by blocking the approach of dicer from the DNA modified end. Fluorine substitution is reported to increase the stability of the RNA strand. The corresponding 5' amino modified products were synthesized and labeled as S1-NH$_2$, S2-NH$_2$, S3-NH$_2$ and A1-NH$_2$. These single stranded RNAs were annealed with their complements for RNAi testing.

Initial RNAi testing shows that the two DNA by at 3'-end of sense strand is important for RNAi efficiency. Fluorine substitution has no impact on the knockdown efficiency as expected. Moreover, amino modification at the 5'-end at either sense or antisense strand was quite tolerable (see biological results section for details). Based on these results, two substrates, S3-NH$_2$ and A1-NH$_2$ were chosen for further modification with linker 23.

Figure 6:
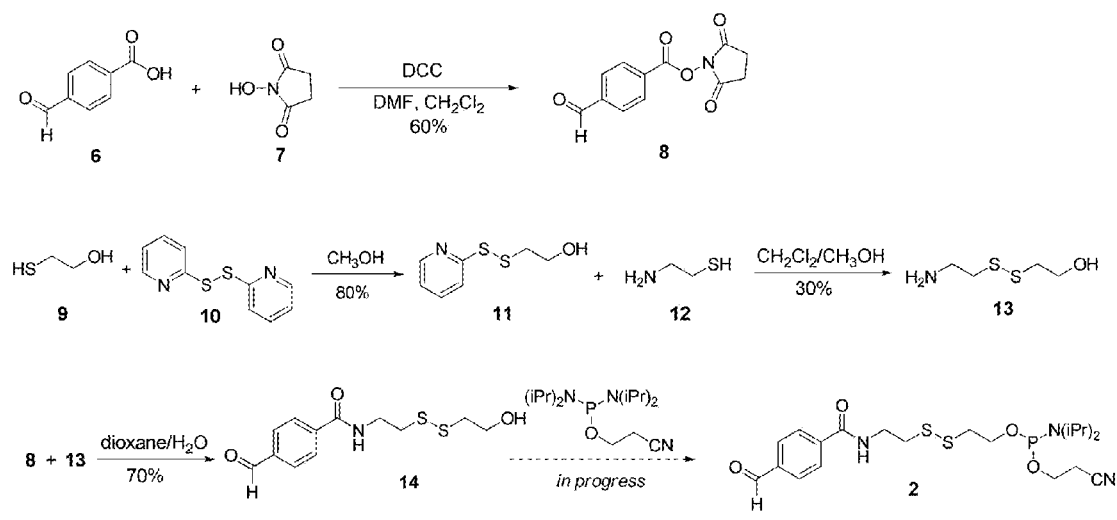
FIG. 6 is a schematic diagram illustrating a synthesis of phosphoramidite 2 according to one embodiment.
Figure 10:
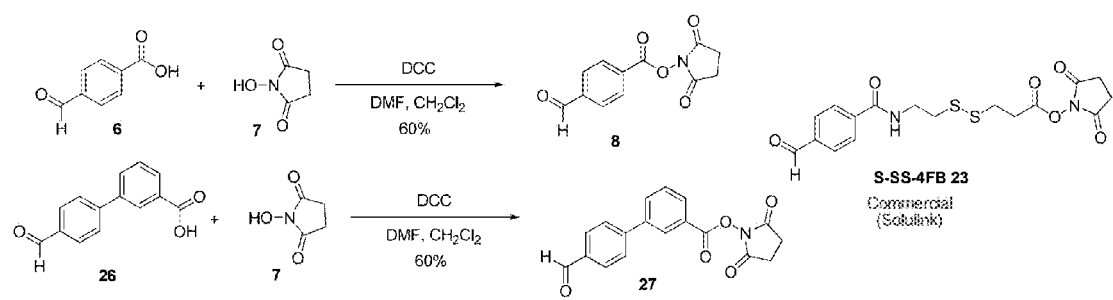
FIG. 10 is a schematic diagram illustrating the chemical equations associated with the synthesis of aldehyde linkers according to some embodiments.

To compare the effects of the modifier on the knockdown efficiency of siRNA, two additional linkers similar to 23 was design and synthesized (FIG. 10). Linker 8 and 27 are non-cleavable versions of the disulfide linker 23. In the synthesis of phophoramidite 2 (FIG. 6), compound 8 was obtained as an intermediate from acid 6 with NHS 7. Similarly, a bulkier linker 27 was synthesized from acid 26.

Figure 11:
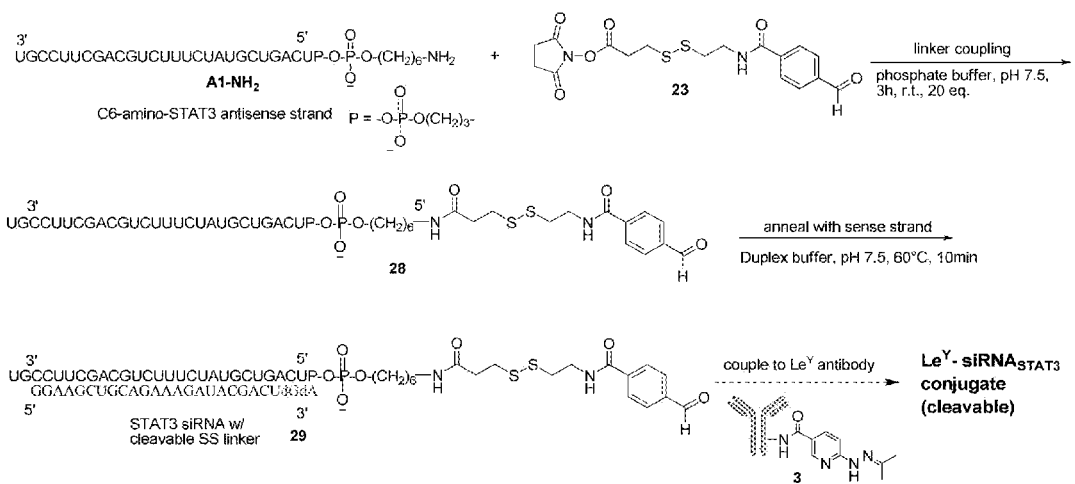
FIG. 11 (SEQ ID NOS: 8 and 1) is a schematic diagram illustrating the chemical equations associated with the synthesis of aldehyde modified siRNA duplex that may be couples to a $Le^Y$ antibody according to some embodiments.

All three linkers were coupled to the RNA single strands S3-NH$_2$ and A1-NH$_2$. FIG. 11 illustrates the reaction sequence using A1-NH$_2$ and linker 23. All other linked RNAs were prepared similarly. Briefly, 5'-amino modified single strand RNA A1-NH$_2$ was allowed to react with the NHS-aldehyde linker 23 to form the aldehyde-modified single stranded RNA 28. The structure of this aldehyde was verified by LTQ-FT mass spectrum. Upon annealing of 28 with its complementary strand to provide the desired siRNA duplex 29, the linker-modified siRNA is ready for antibody conjugation. The reaction conditions for the coupling reaction with linker were optimized by monitoring the extent of the reaction by HPLC (data not shown). A 20-fold excess of linker to RNA is necessary to obtain high yields. Because the existence of the aldehyde group and/or disulfide bond, temperature stability of aldehyde-disulfide modified single strand was verified by LTQ-FT mass spectral analysis (FIG. 12). At 60° C. for 40 min, modified RNA did not show degradation; at higher temperature (90° C.) decomposition was observed by the appearing of fragmented signals in the mass spectrum. Thus, 60° C. for 10 min was used for the annealing of the aldehyde linked RNA with its complementary strand.

Figure 18:
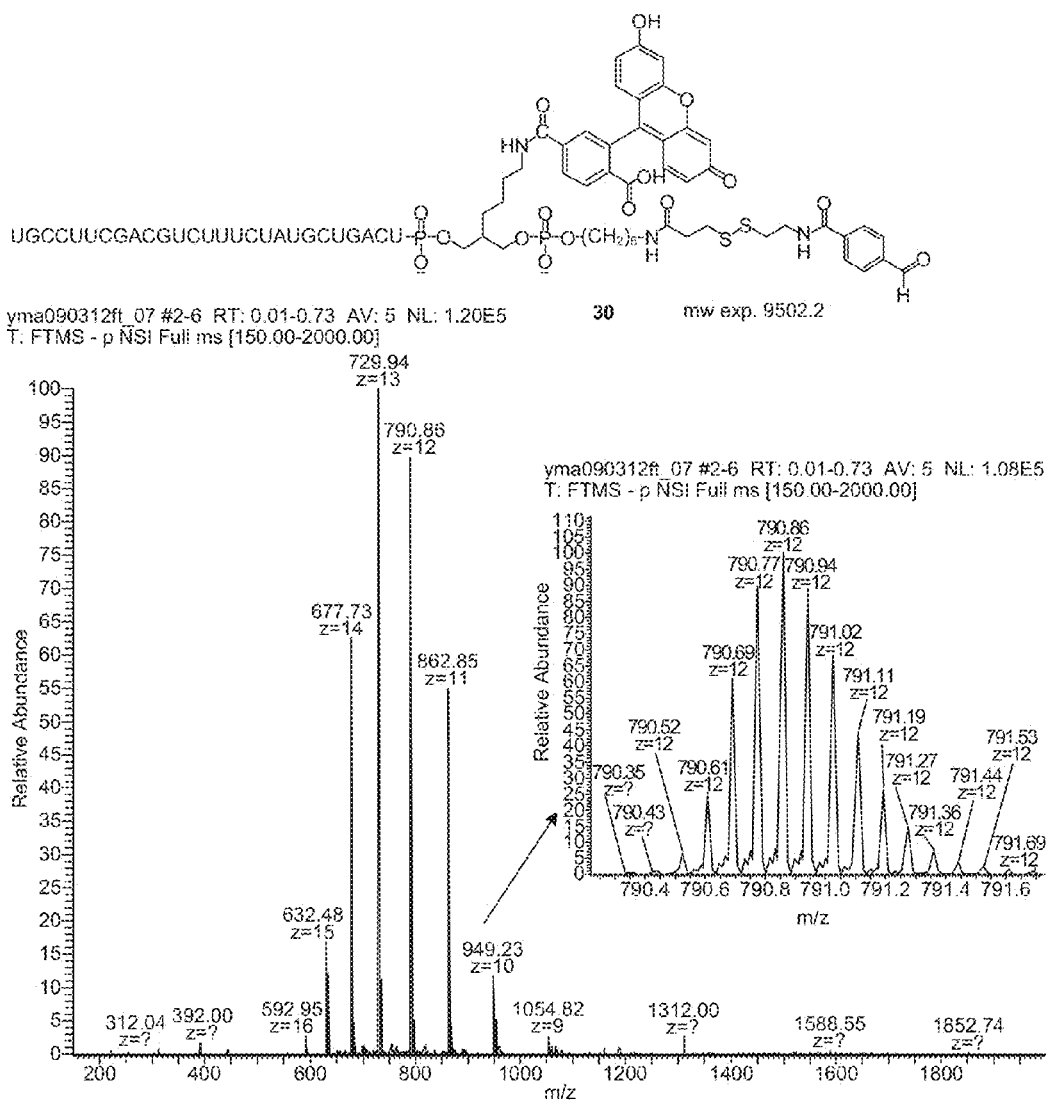
FIG. 18 (SEQ ID NO: 8) is an LTQ-FT mass spectrum confirming the identity of FAM-labeled RNA antisense strand 30 according to one embodiment.
Figure 32:
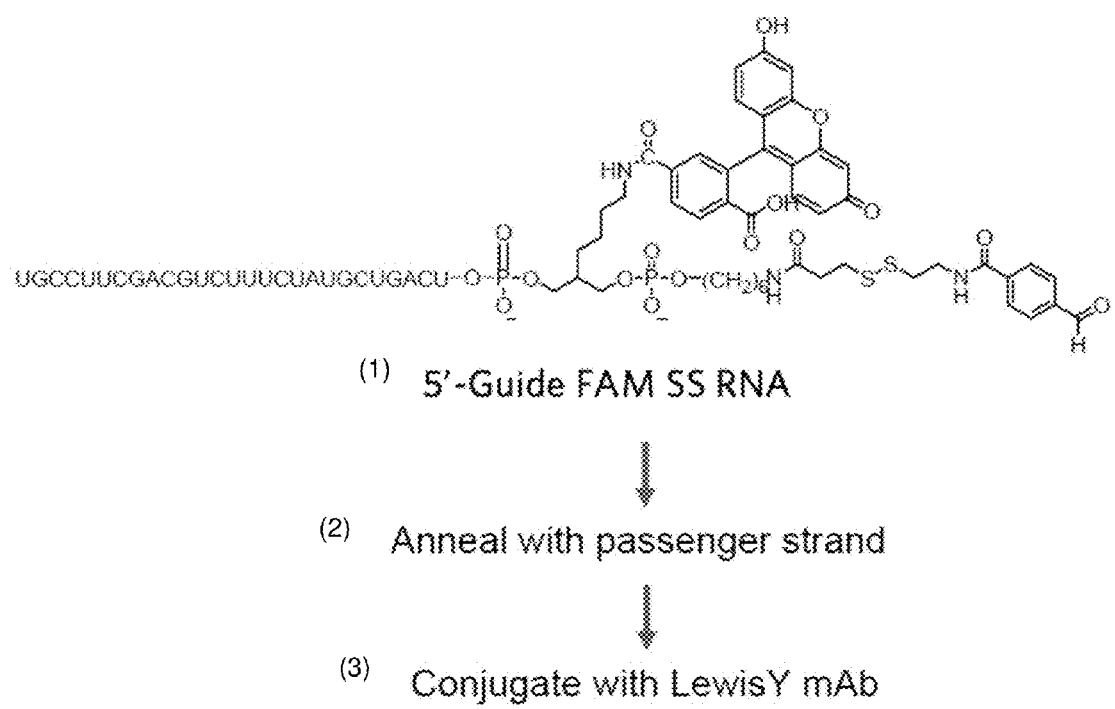
FIG. 32 (SEQ ID NO: 8) shows a 5' FAM-labeled antisense ("guide") strand (1) that may be annealed with a sense ("passenger") strand (2) and then conjugated to a a $Le^Y$ antibody (3).

In addition, to gain a better understanding of the internalization of the antibody-siRNA conjugate, siRNA fluorescently labeled with 5 carboxy-fluorescein (FAM) was prepared and conjugated with Hu3S193 using the same methodology as describe above. The structure of the FAM labeled antisense strand 30 (FIG. 32) was verified by LTQ-FT mass spectroscopy as depicted in FIG. 18.

RNAi knockdown efficiency results (see Biological Results Section) show that the modification with aldehyde was tolerable for both the cleavable and non-cleavable linker versions; however, the bulkier non-cleavable linker 27 attached at 5' end on the sense strand caused a reduction in the knockdown efficiency. One possible explanation is the steric hindrance of this larger sized linker hinders the approach of the dicer complex. Again, the fluorine substitution does not influence the knockdown efficiency. Given these results, antisense 5' modification 28 and non-fluorine substituted sense strand were used with two DNA by at the 3' end of S1 for the initial studies regarding antibody conjugation and biological testing.

Construction of Linker-modified hu3S193

Figure 13:
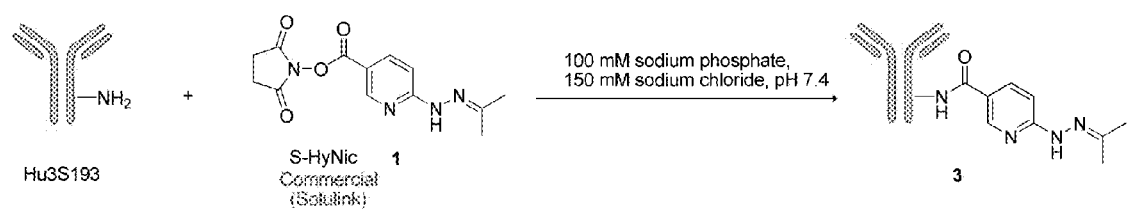
FIG. 13 is a schematic diagram illustrating the chemical equation associated with modification of Hu3S193 with S-HyNic according to some embodiments.

After synthesizing the siRNA aldehyde 29 as described above, hu3S193 was modified with S-HyNic in preparation to couple with siRNA 29 (FIG. 13).

Figure 14:
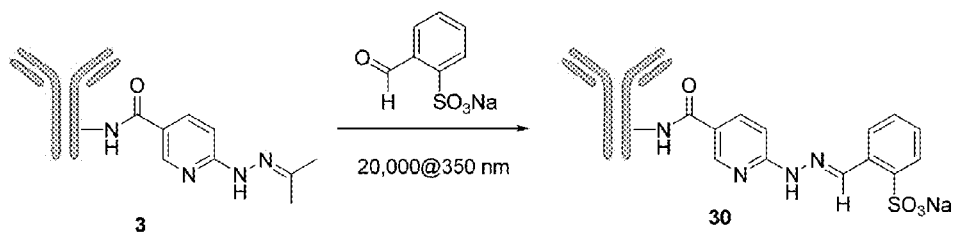
FIG. 14 is a schematic diagram illustrating the chemical equation associated with molar substitution ratio (MSR) determination according to some embodiments.

The molar substitution ratio (MSR) of hydrazine linker 3 to antibody was determined using 2-sulfobenzaldehyde (FIG. 14). Specific UV absorbance of the resulting bis-arylhydrazone at 350 nm with a molar extinction coefficient 20,000 L/mol.cm was used in calculations. The results with different protein concentrations and linker ratios are listed in Table 1, below. For the initial study, a protein concentration with 3 mg/mL and a 20-fold molar excess of linker was used to obtain a reasonable conjugation yield without introducing excessive amounts of modification on the antibody. This approach provides the use of different conjugation ratios for further study if necessary.

TABLE 1

MSR of S-HyNic on Hu3S193.

| | Ab concentration (mg/mL) | | | | | |
|---|---|---|---|---|---|---|
| | 3 | 3 | 3 | 10 | 10 | 5 | 5 |
| S-HyNic/Hu3S193 | 20 | 14 | 7 | 20 | 5 | 10 | 5 |
| Molar Substitution Ratio | 4.2 | 2.1 | 1.9 | 7.1 | 5.0 | 3.2 | 1.9 |

Conjugation of Linker-modified Target siRNA to Linker-Modified hu3S193

Figure 15:
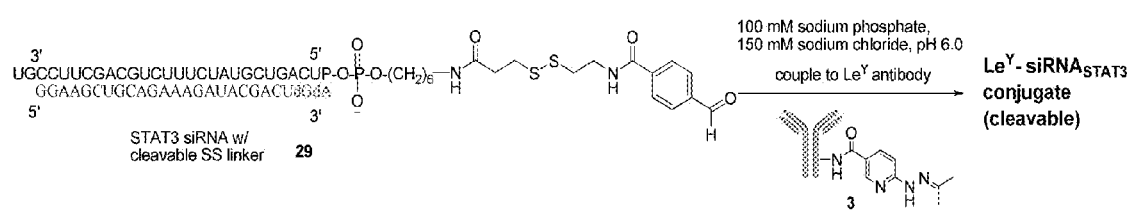
FIG. 15 (SEQ ID NO: 8 and 1) is a schematic diagram illustrating the chemical equation associated with the conjugation reaction of modified siRNA 29 with modified Hu3S193 3.
Figure 16A:
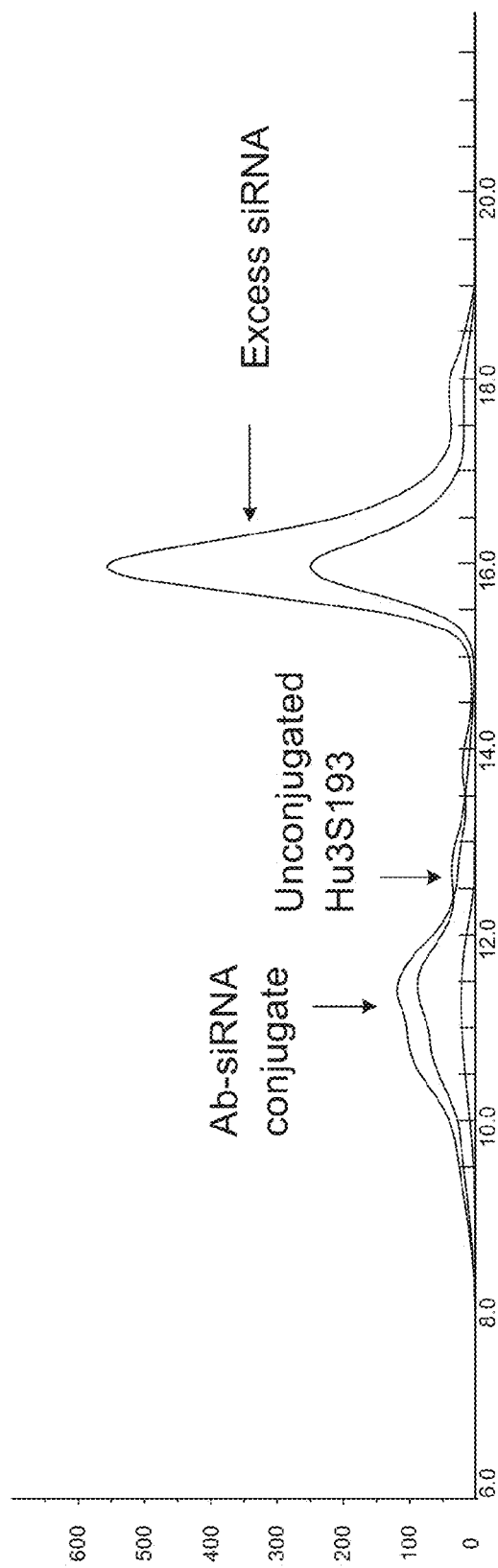
FIG. 16 is a set of graphs showing the results of a fast protein liquid chromatography (FPLC) analysis. FPLC was carried out in PBS buffer using Superdex 200 10/300 GL column on an ÄKTAFPLC system (GE Healthcare, previously Amersham Biosciences) at 4° C., flow rate 0.5 mL/min. (A) is the whole spectrum showing all fractions. (B) Shows the protein potion of the FPLC trace. (C) Shows the wild type hu3S193 portion of the FPLC trace. Detection, Top line, 254 nm; middle line, 280 nm; bottom line, 354 nm (Y-axis is doubled-expanded for clarity). Retention volume: A2, 10.3 mL, A3, 10.8 mL, A4, 11.3 mL, A5, 11.8 mL, A6, 12.3 mL, A7, 12.8 mL and A14, 16.3 mL.
Figure 16B:
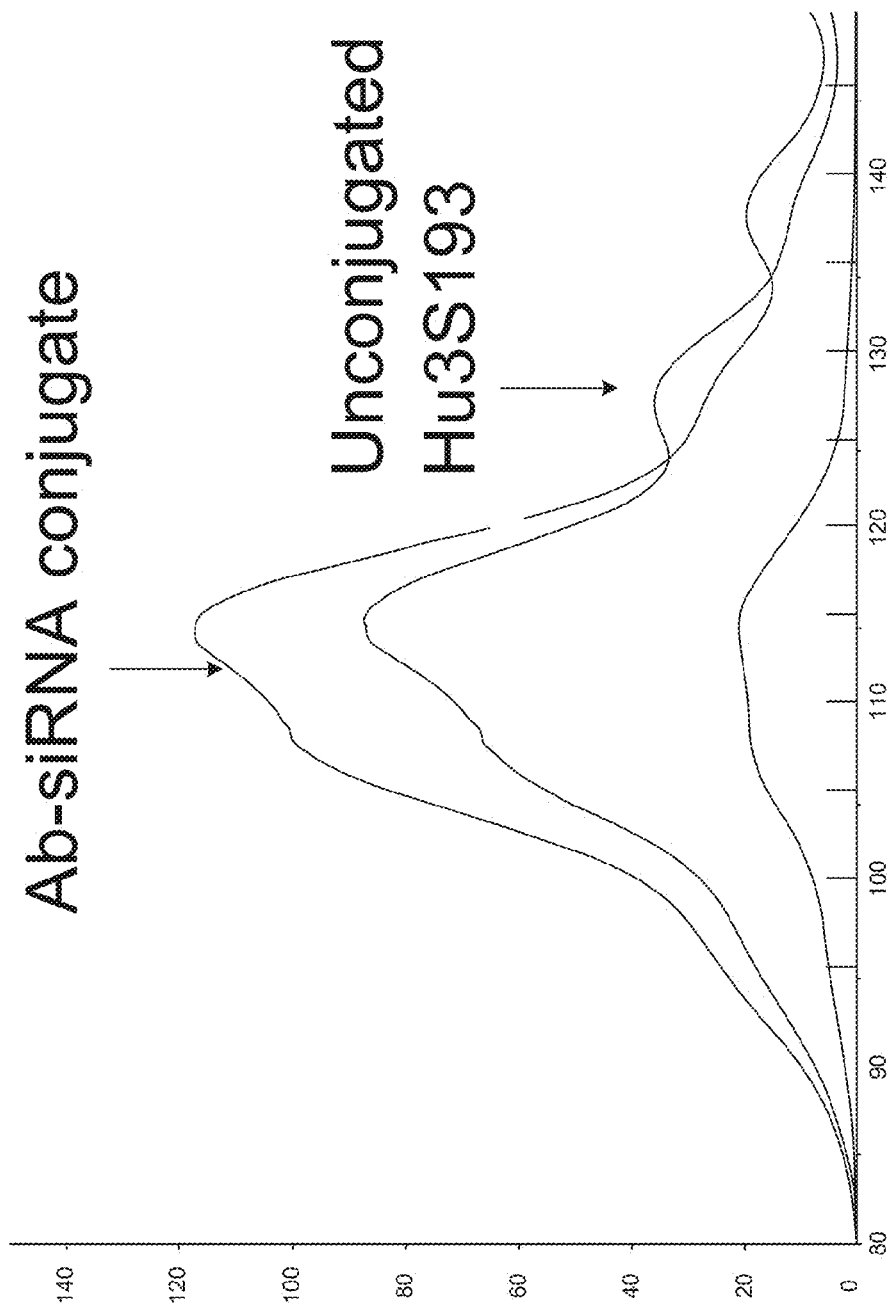
Figure 16C:
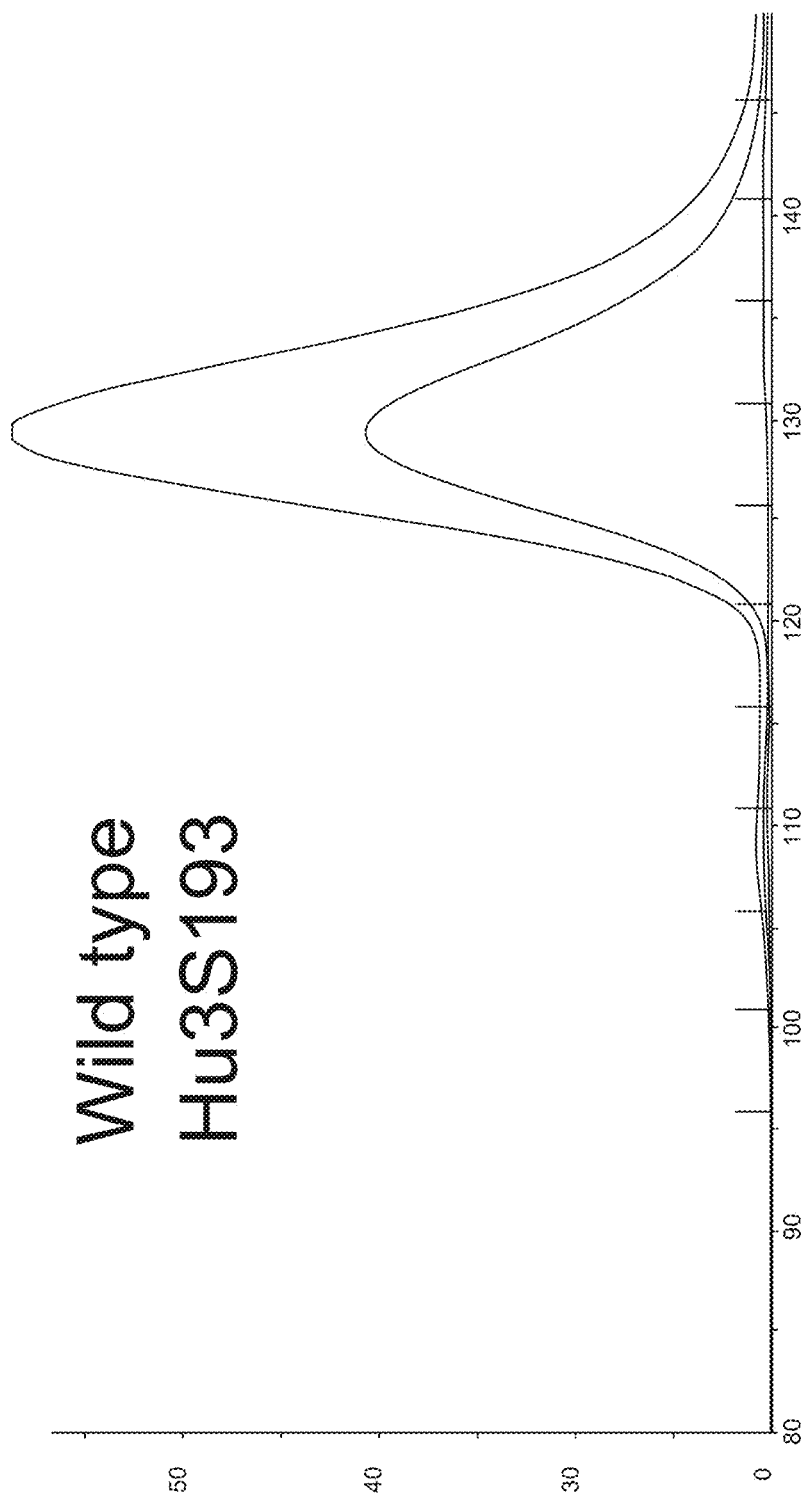

Next, S-HyNic modified Hu3S193 3 was conjugated to aldehyde-disulfide modified STAT3 siRNA 29 (FIG. 15). The conjugation was carried at either 4° C. or room temperature with a 5 fold siRNA/antibody ratio. FPLC results did not show an obvious difference. The conjugation mixture was FPLC purified under nuclease free condition. Unreacted excess siRNA (fraction A14, retention volume 16.3 mL) was easily separated from the antibody conjugate by FPLC (FIG. 16A). Antibody-siRNA conjugate fractions (A2-A6) were identified by the specific UV absorbance at 354 nm which represents the newly formed bis-arylhydrazone bond (FIGS. 16A and B). Small amounts of unconjugated antibody fractions (A7) matches the retention volume (12.8 mL) of wild type Hu3S193 (FIG. 16C). This fraction does not have the hydrazone UV signature absorbance at 354 nm.

Figure 17:
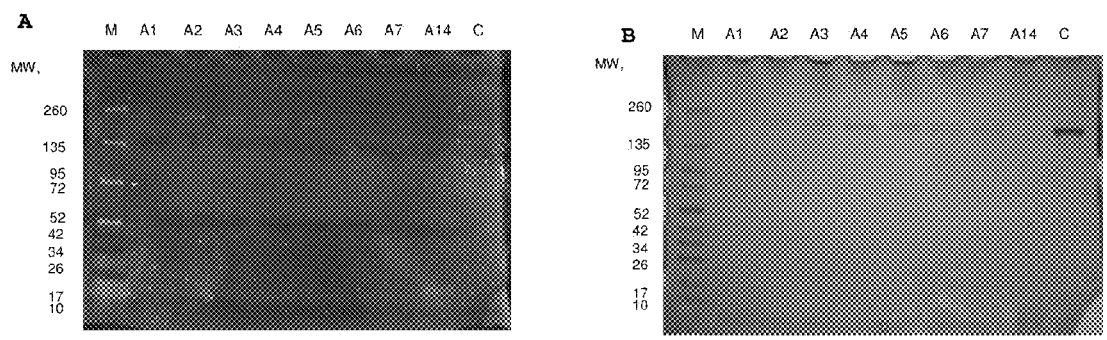
FIG. 17 shows non-reducing SDS-PAGE results of FPLC fractions. Non-reducing SDS-PAGE with 4-15% Ready Gel Tris-HCl Gel (no DTT). (A) Gel stained with SYBR® Gold Nucleic Acid gel stain. (B) Gel stained with simplyBlue™ SafeStain. Observed under AlphaImager®. M: Markers. A1-A14: FPLC fractions, C1: HyNic modified antibody. All samples incubated at 37° C. with LDS loading buffer before loading.

Fractions were checked by non-reducing SDS-PAGE directly after FPLC. In order to determine the best gel running conditions, samples were incubated with loading buffer (no-reducing agents) at room temperature, 37° C., 60° C. or 90° C. for 5 min before loading. Optimal results were obtained at 37° C. Non-reducing SDS-PAGE results of FPLC fractions matches the FPLC prediction of the antibody-conjugate (FIG. 17). Fraction A2-A6 represents mAb-siRNA conjugates. These all showed greater staining with SYBR® Gold which stains nucleic acids compared to fraction A7 which does not have conjugated siRNA. In addition, all fractions showed similar staining intensities with coomassie blue which is a protein specific stain. All fractions from A2 to A6 migrate slower compared to A7 and linker modified Hu3S193 3. Fractions A2 and A4 may correspond to different ratios of conjugate to siRNA.

The conjugation ratio of siRNA/antibody was calculated from the concentration of protein and UV absorbance of siRNA at 260 nm. The concentration of protein in each fraction was obtained from a Bradford assay under the assumption that it should not be influenced by the siRNA component of the conjugate. Because the antibody also has contributes to UV absorbance at 260 nm, a correction was done using the flowing equation $A260_{siRNA} = A260_{total} - A280_{Ab} \times 0.67$. A280 of antibody was back calculated from the concentration of protein using the calculated absorbance value of 1.36 absorbance units/mg of protein. The relative ratio of $A260_{Ab}$ to $A280_{Ab}$ is 0.67 in the same buffer system. Calculated results from the Bradford assay and UV260 is listed in Table 2 below. The major product was determined to be a 1:1 ratio of siRNA/antibody with the minor product being a 2:1 ratio of siRNA/antibody.

TABLE 2

Conjugation efficiency and siRNA/Hu3S193 ratio.

| | A2 | A3 | A4 | A5 |
|---|---|---|---|---|
| Ab (ug/mL) | 140.22 | 229.89 | 252.81 | 284.69 |
| Ab (nmole/mL) | 0.71 | 1.17 | 1.43 | 1.61 |
| A260 (total) | 0.90 | 0.86 | 0.94 | 1.06 |
| A260 of antibody | 0.13 | 0.21 | 0.23 | 0.26 |
| A260 of siRNA | 0.77 | 0.65 | 0.71 | 0.80 |
| amount of siRNA (nmole/mL) | 1.50 | 1.26 | 1.38 | 1.55 |
| siRNA/antibody | 2.11 | 1.08 | 0.96 | 0.97 |

Figure 31:
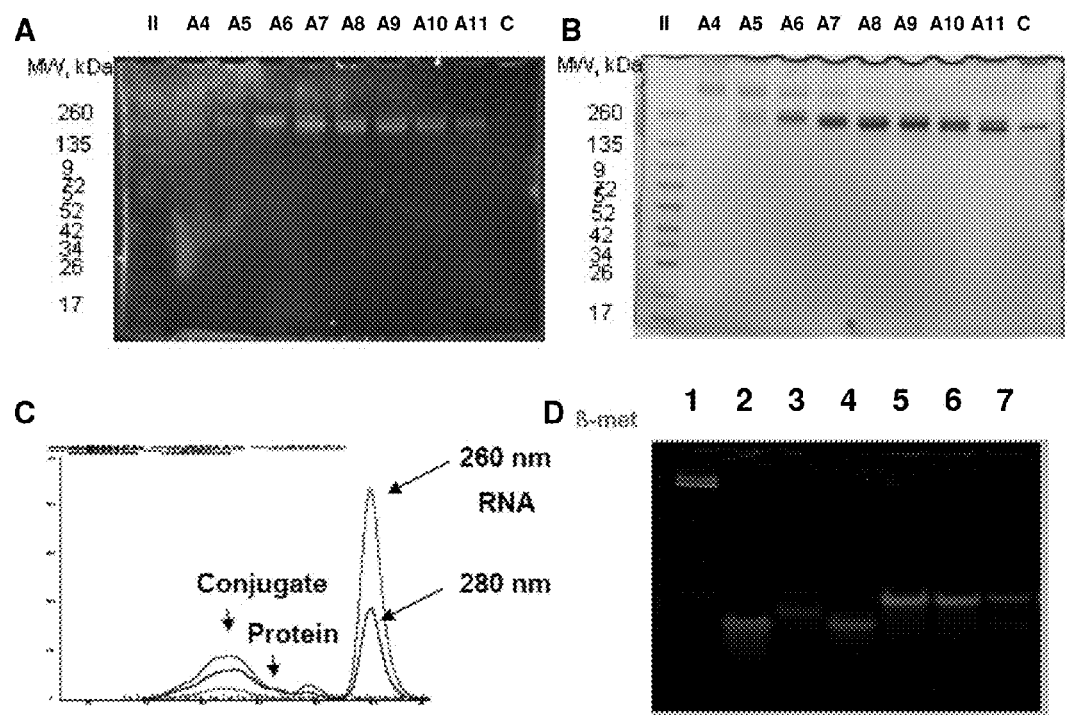
FIG. 31 illustrates the confirmation of the covalent construct 28. (A) and (B) illustrate SDS-PAGE gels from the M (marker), A4-A11 and C (hu3S193) antibody with SYBR® Gold (siRNA) staining (A), SimplyBlue™ SafeStain (mAb), fast protein liquid chromatography (FPLC) traces (left arrow mAb-siRNA, right arrow unconjugated mAb) (C) and PAGE stained with SYBR® Gold (1=untreated conjugate, 2-4=single strand siRNA, 5=DTT treated conjugate (broken at disulfide bond) and 6-7=double stranded siRNA.

The identity covalent construct was confirmed by purifying by FPLC followed by analysis by non-reducing SDS-PAGE (FIG. 31). The product showed a signal of both RNA and protein (FIGS. 31A-B), has a higher molecular weight than unmodified mAb (FIG. 31C) and can be reduced by dithiothreitol (DTT) due to disulfide linker and product corresponding to the siRNA component (FIG. 31D).

Figure 19A:
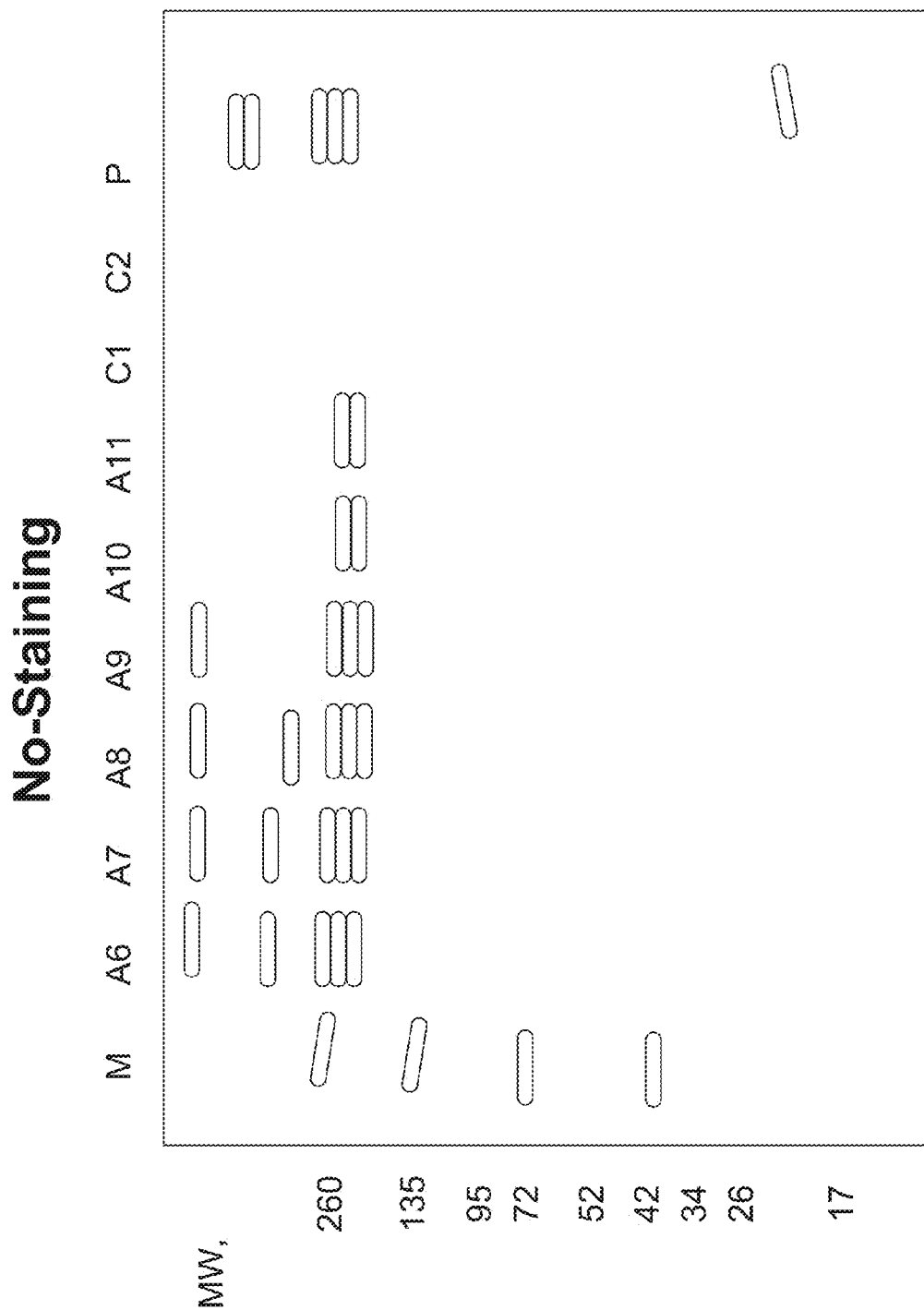
FIG. 19 shows the results of fluorescently labeled siRNA-antibody gel and FPLC. A-C, Non-reducing SDS-PAGE (no DTT). (A) No-stain, 365 UV, EtBr filter, Observed under EpiChemi™ II Darkroom. (B) Gel stained with SYBR® Gold Nucleic Acid Gel Stain Observed under EpiChemi™ II Darkroom. (C) Gel then stained with simplyBlue™ SafeStain. Scanned by EPSON PEFECTION V750 PRO. M: Markers. A6-A11: antibody-siRNA FPLC fractions. P: mixture before FPLC purification. C1: HyNic modified antibody. C2: wild type antibody. All samples warm at 37° C. with Laemmli sample buffer before loading. (D) FPLC trace of corresponding fractions. Detection, red line, 254 nm; blue line, 280 nm; purple line, 354 nm (Y-axis doubly-expanded for clarity). Retention volume: A6, 10.0 mL, A7, 10.5 mL, A8, 11.0 mL, A9, 11.5 mL, A10, 12.0 mL, A11, 12.5 mL.
Figure 19B:
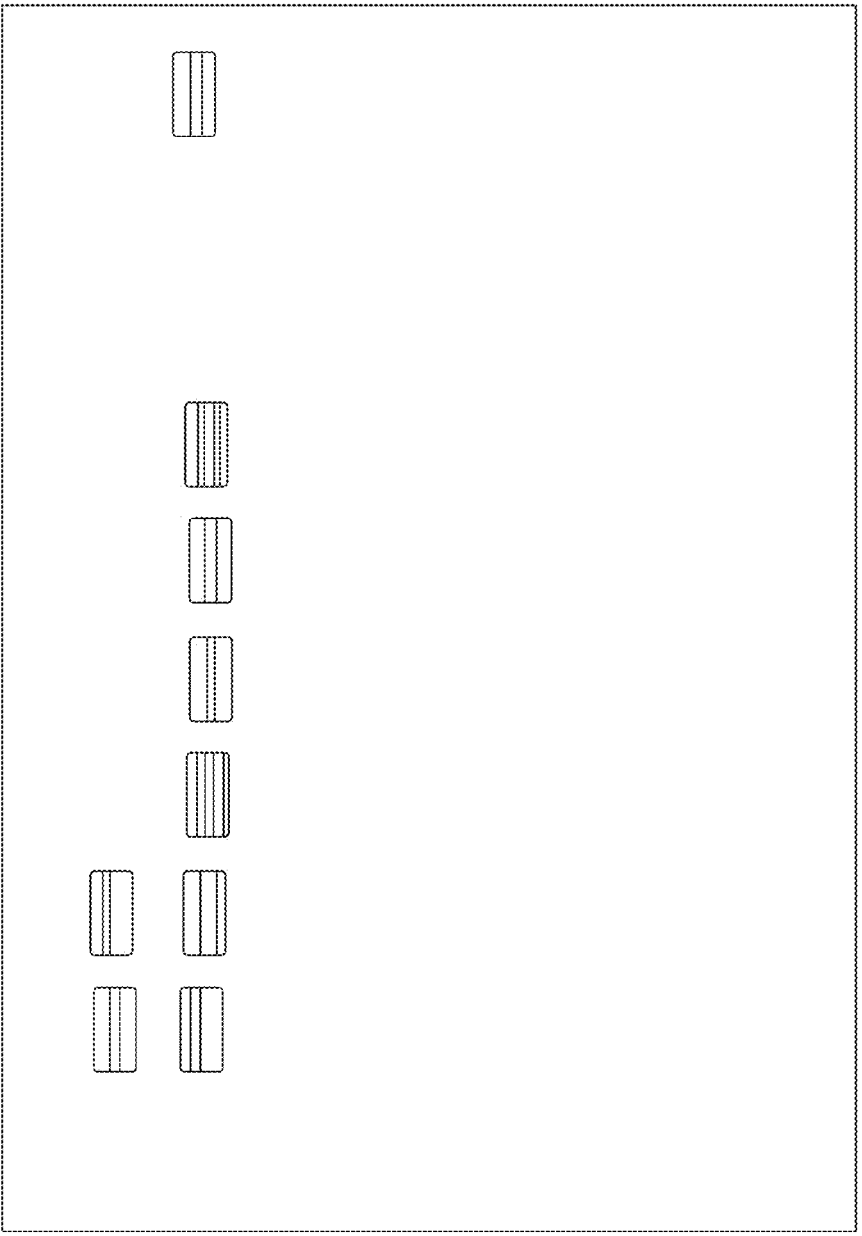
Figure 19C:
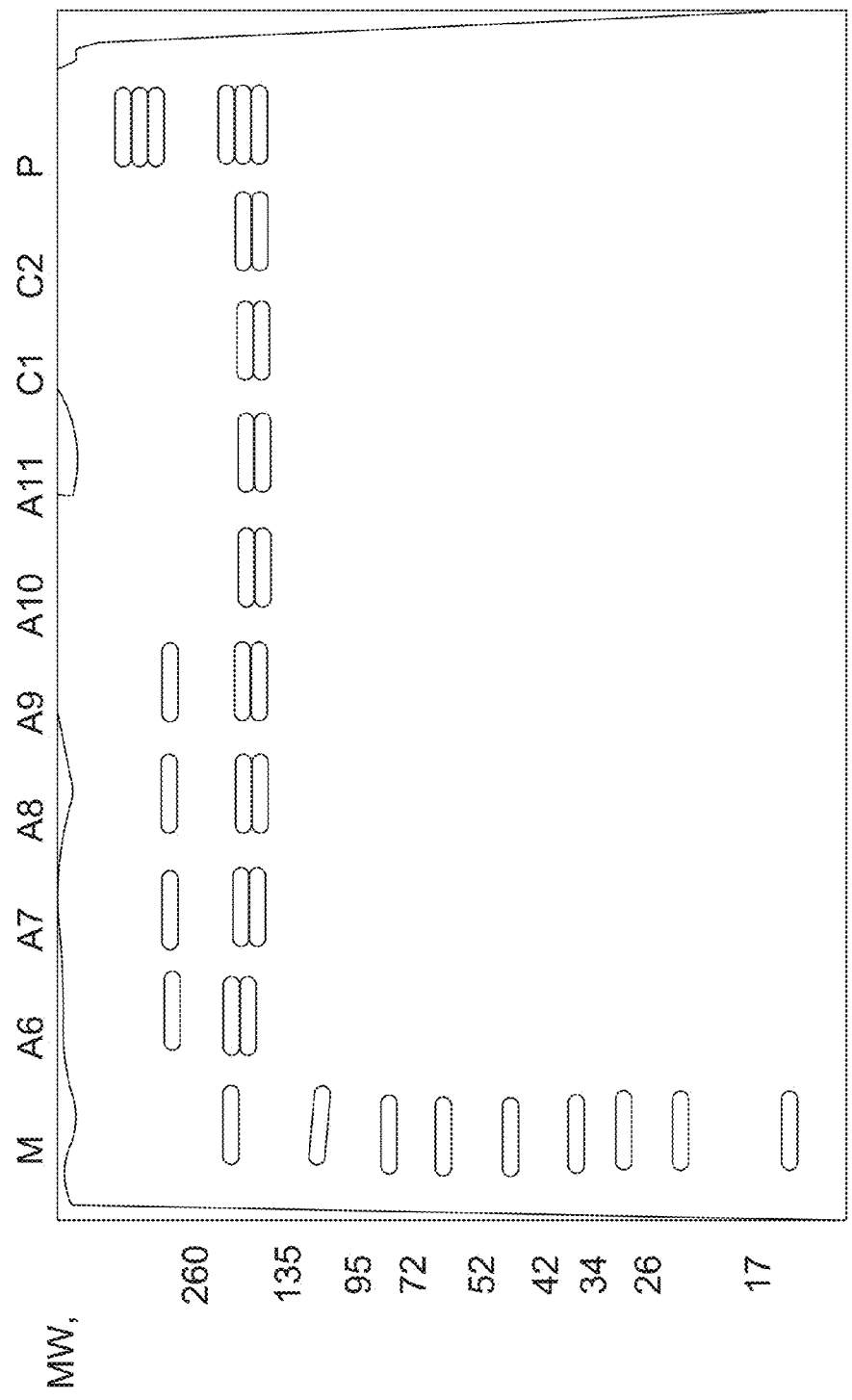
Figure 19D:
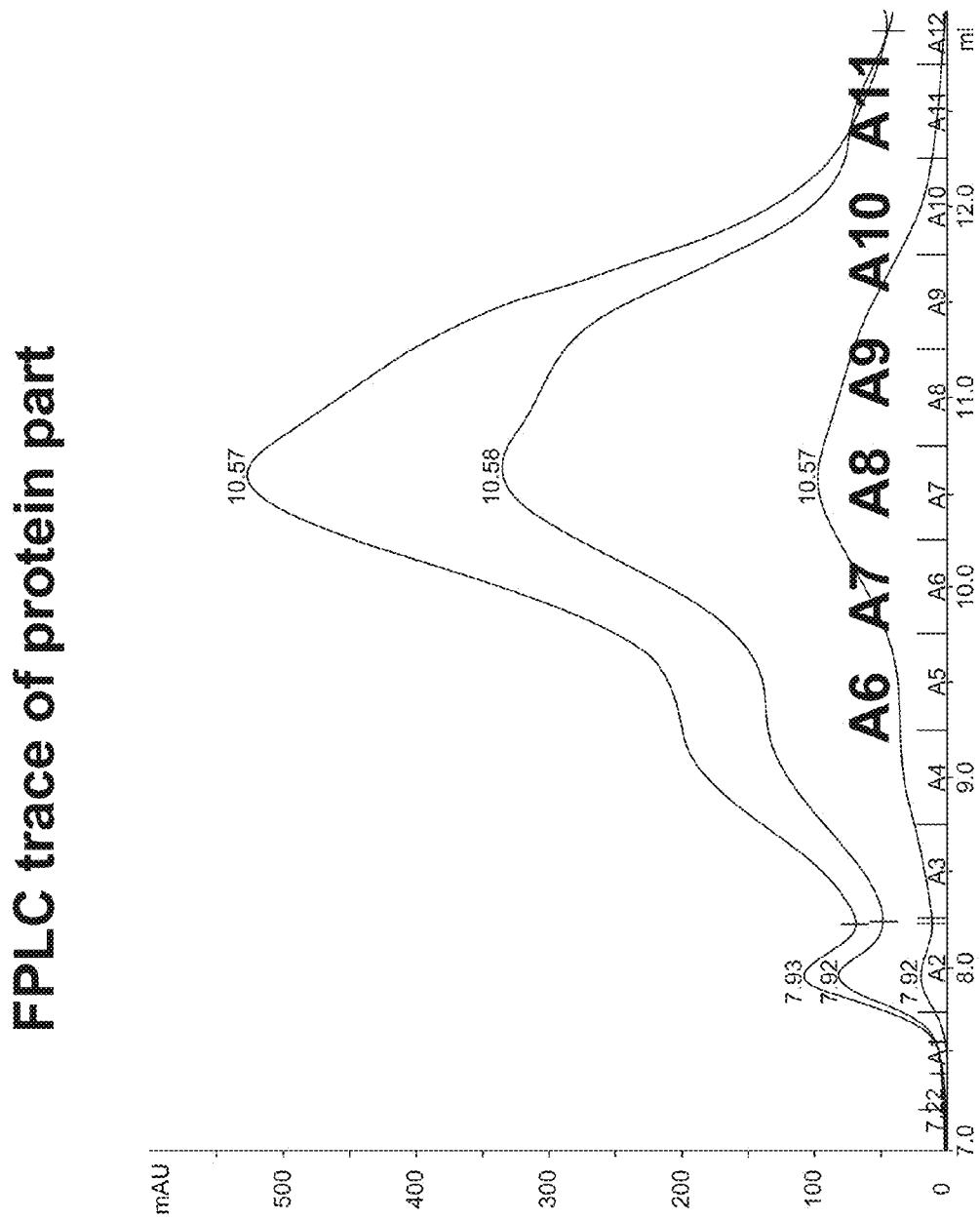

Analogously, the antibody-siRNA-FAM conjugate was purified by FPLC (see FIG. 19D for FPLC trace) and analyzed by non-reducing SDS-PAGE. Observation of the gel under UV light (no staining) clearly shows the fluorescence signal (FIG. 19A). SYBR® Gold staining (FIG. 19B) shows the same results as the non-staining one. Coomassie blue staining shows the slower migration of fractions comparing with wild type hu3S193 (FIG. 19C). Antibody concentration and siRNA/antibody ratio was measured as described above. Results are listed in Table 3.

TABLE 3

Conjugation efficiency and FAM labeled siRNA/Hu3S193 ratio.

| | A6 | A7 | A8 | A9 | A10 | A11 |
|---|---|---|---|---|---|---|
| Ab (ug/mL) | 599.25 | 853.93 | 719.10 | 737.83 | 606.74 | 385.77 |
| Ab (nmole/mL) | 3.04 | 4.33 | 3.85 | 3.95 | 3.43 | 2.18 |
| Ab (280) | 0.81 | 1.16 | 0.98 | 1.00 | 0.83 | 0.52 |
| Ab (260) | 0.55 | 0.78 | 0.66 | 0.67 | 0.55 | 0.35 |
| siRNA (260) | 3.09 | 4.42 | 2.86 | 2.57 | 1.49 | 1.00 |
| siRNA (nmole/mL) | 5.77 | 8.25 | 5.34 | 4.79 | 2.77 | 1.86 |
| siRNA/Ab | 1.90 | 1.90 | 1.39 | 1.21 | 0.81 | 0.85 |

Figure 33:
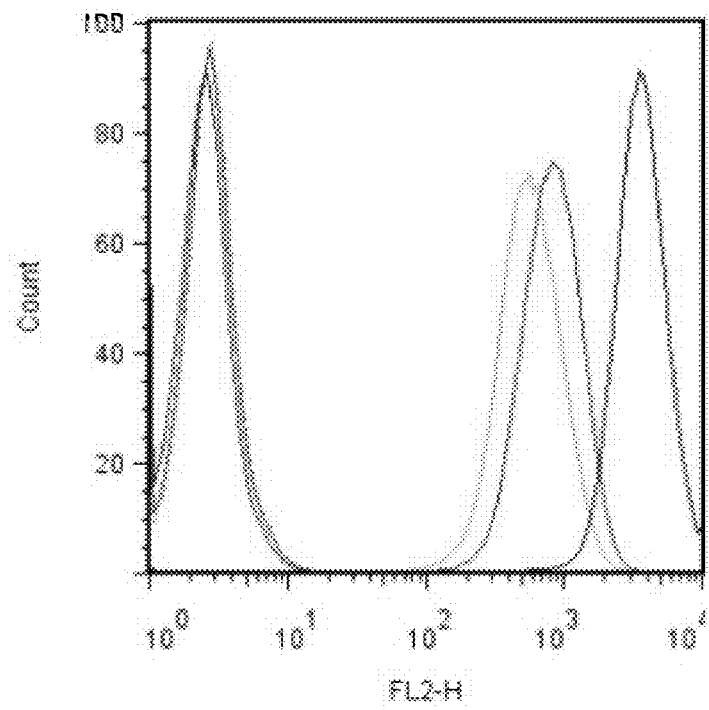
FIG. 33 shows results of a flow cytometry that illustrates that the mAb-siRNA construct (hu3S193-siRNA) retains the mAb's binding affinity to the $Le^Y$ antigen in antigen positive cells (A431 cells).

Retention of mAb Binding Affinity and Specific Binding to Target Cells by the hu3S193-siRNA Complex A fluorescence-activated cell sorting (FACS) analysis using fluorescently labeled siRNA was performed to analyze binding affinity of the hu3S193 antibody with or without conjugation to the siRNA (FIG. 33). The results of the FACS analysis are shown in Table 4 below. Even with reduced binding affinity of the mAb-siRNA construct compared to unmodified hu3S193, significant shifts were still observed for mAb-siRNA conjugates to antigen positive cells compared to negative controls (FIG. 33).

TABLE 4

FACS analysis of Le^Y negative (MDA-MB-435) and Le^Y positive (A431) cells

|  | MDA-MB-435 (Le$^{Y-}$) | A431 (Le$^{Y+}$) |
|---|---|---|
| Le$^Y$ expression | 4% | 98% |
| siRNA alone | 1% | 1% |
| Hu3S193-siRNA (covalent | 4% | 67% |

EXAMPLE 2

Selection of Linker-modified Target siRNA

To determine the optimal design for the mAb-STAT3 siRNA conjugate the influence of several modifications on the STAT3 knockdown efficiency were evaluated, including the attachment site of the linker (5' end of sense strand or 5' end of antisense strand), the addition of DNA bases (versus all RNA bases) at the 3' end of the sense strand and incorporation of 2'FU and 2'FC in the sense strand and type of linker (cleavable versus non-cleavable).

The following negative control siRNA, STAT3 siRNA, and linker-STAT3 siRNA constructs (Table 5) were transfected into DU-145 cells at a concentration of 50 nM using a cationic lipid (RNAiMAX, Invitrogen, Carlsbad, Calif.).

TABLE 5

Linker-STAT3 siRNA constructs.

| | | SEQ ID NO: |
|---|---|---|
| Negative control | CUUCCUCUCUUUCUCUCCCUUGUdGdA-3'<br>3'-AGGAAGGAGAGAAAGAGAGGGAACA C U | 9<br>10 |
| Positive control (AD) | GGAAGCUGCAGAAAGAUACGACUdGdA-3'<br>3'-UGCCUUCGACGUCUUUCUAUGGUGA C U | 11<br>12 |
| BD | GGAAGCUGCAGAAAGAUACGACUGA-3'<br>3'-UGCCUUCGACGUCUUUCUAUGGUGACU | 13<br>14 |
| CD | GGAAG<u>fCfUGfC</u>AGAAAGA<u>fUAfC</u>GA<u>fCfU</u>dGdA-3'<br>3'-UGCCUUC G AC GUCUUUCU AU GGU GA C U | 15<br>16 |
| ED | H$_2$N—(CH$_2$)$_6$—O—P(=O)(O$^-$)—O—(CH$_2$)$_3$—O—P(=O)(O$^-$)—O—<br>GGAAGCUGCAGAAAGAUACGACUdGdA-3'<br>3'-UGCCUUCGACGUCUUUCUAUGGUGA C U | 17<br>18 |
| FD | H$_2$N—(CH$_2$)$_6$—O—P(=O)(O$^-$)—O—(CH$_2$)$_3$—O—P(=O)(O$^-$)—O—<br>GGAAGCUGCAGAAAGAUACGACUGA-3'<br>3'-UGCCUUCGACGUCUUUCUAUGGUGACU | 19<br>20 |
| GD | H$_2$N—(CH$_2$)$_6$—O—P(=O)(O$^-$)—O—(CH$_2$)$_3$—O—P(=O)(O$^-$)—O—<br>GGAAG<u>fCfUGfC</u>AGAAAGA<u>fUAfC</u>GA<u>fCfU</u>dGdA-3'<br>3'-UGCCUUC G AC GUCUUUCU AU GGU GA C U | 21<br>22 |
| AH | H$_2$N—(CH$_2$)$_6$—O—P(=O)(O$^-$)—O—(CH$_2$)$_3$—O—P(=O)(O$^-$)—O—<br>U CAGUCGUAUCUUUCUGCAGCUUCCGU-3'<br>3'-dAdGUCAGCAUAGAAAGACGUCGAAGG | 23<br>24 |
| BH | H$_2$N—(CH$_2$)$_6$—O—P(=O)(O$^-$)—O—(CH$_2$)$_3$—O—P(=O)(O$^-$)—O<br>UCAGUCGUAUCUUUCUGCAGCUUCCGU-3'<br>3'-AGUCAGCAUAGAAAGACGUCGAAGG | 25<br>26 |

TABLE 5-continued

Linker-STAT3 siRNA constructs.

| | SEQ ID NO: |
|---|---|

CH

H$_2$N—(CH$_2$)$_6$—O—P(O$^-$)(=O)—O—(CH$_2$)$_3$—O—P(O$^-$)(=O)—O

```
      U  C  A GUC GU AUCUUUCU GC AGCUUCCGU-3'            27
3'-dAdGfUfCAGfCAfUAGAAAGAfCGfUfCGAAGG                    28
```

DNA bases are in bold, 2'FU and 2'FC are underlined.

The transfection efficiency was >90%, as determined by FACS analysis of cells transfected with 50 nM Cy3-labeled negative control siRNA. The RNA was isolated 24 h after transfection and the knockdown efficiencies were determined by qPCR. The qPCR data were analyzed using the delta-delta (ΔΔ) ct method.

Influence of Linker Attachment Site on Knockdown Efficiency

Figure 20:
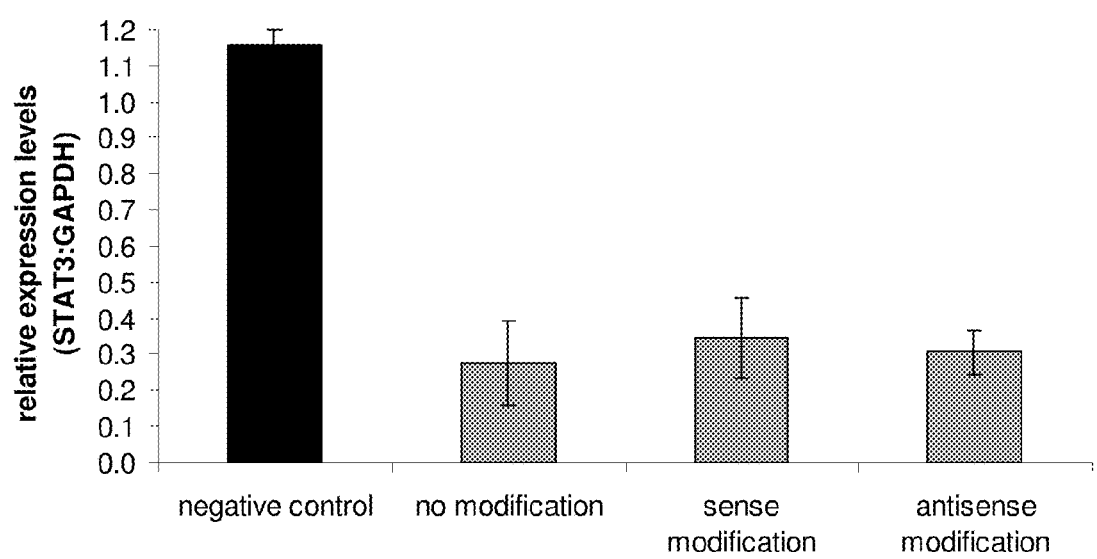
FIG. 20 is a bar graph illustrating the knockdown efficiency of 5'-modified STAT3 siRNAs (sense modification and antisense modification) as compared to no modification.

Since the attachment site of the linker may influence the knockdown efficiency of the siRNA by interfering with dicer we compared the knockdown efficiencies of unmodified siRNA (AD) and linker-siRNA constructs with 5' modified sense (ED) or 5' modified antisense strands (AH). As shown in FIG. 20, STAT3 expression levels decreased about 70% after transfection of unmodified or 5' end modified siRNAs, indicating that the attachment site did not significantly influence the knockdown efficiency of the modified siRNAs.

Two DNA Bases Versus all RNA Bases at the 3' End of the Sense Strand

Figure 21:
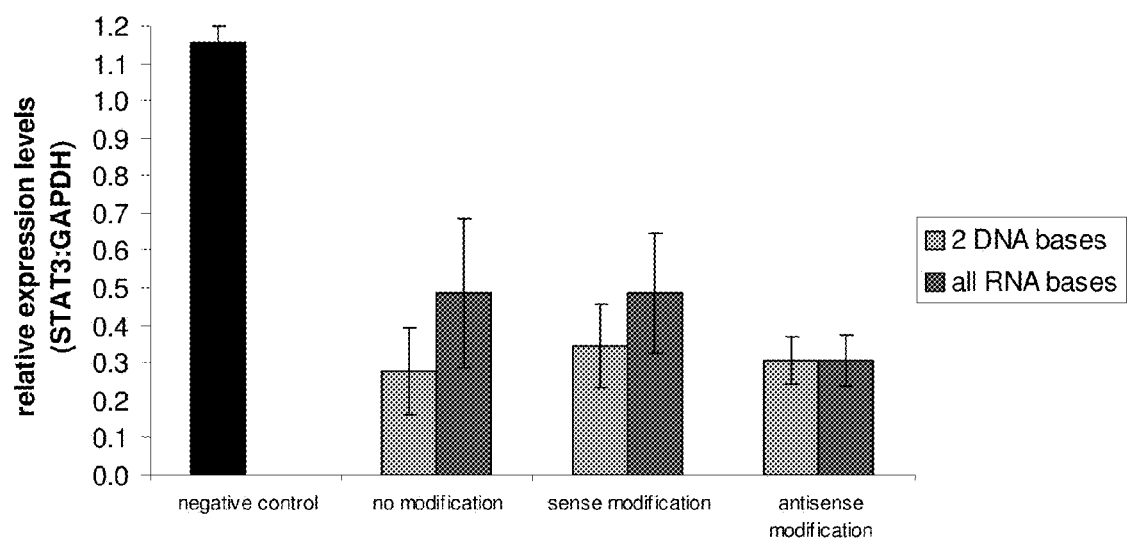
FIG. 21 is a bar graph illustrating the influence of 2 DNA bases incorporated at the 3' end of sense strand on STAT3 knockdown efficiency of 5'-modified STAT3 siRNAs (sense modification and antisense modification) as compared to no modification.

To test whether the knockdown efficiency is improved by the incorporation of 2 DNA bases at the 3' end of the sense (or "passenger") strand we compared the knockdown efficiencies of AD and BD (no 5' modification, with and without DNA bases at the 3' sense end), ED and FD (5' sense strand modified siRNAs with and without DNA bases at the 3' sense end), AH and BH (5' antisense (or "guide") modified siRNA with and without DNA bases at the 3' sense end). The qPCR results show that incorporation of 2 DNA bases at the 3' end of the sense strand either slightly improved the knockdown efficiency (no modification and 5' sense modification) or had no influence on the knockdown efficiency (5' antisense modified siRNAs) (FIG. 21). Based on these results, we will incorporate 2 DNA bases at the 3' end of the sense strand in the final design of the Lewis Y mAb-siRNA conjugate.

Incorporation of 2'FU and 2'FC in the Sense Strand

Figure 22:
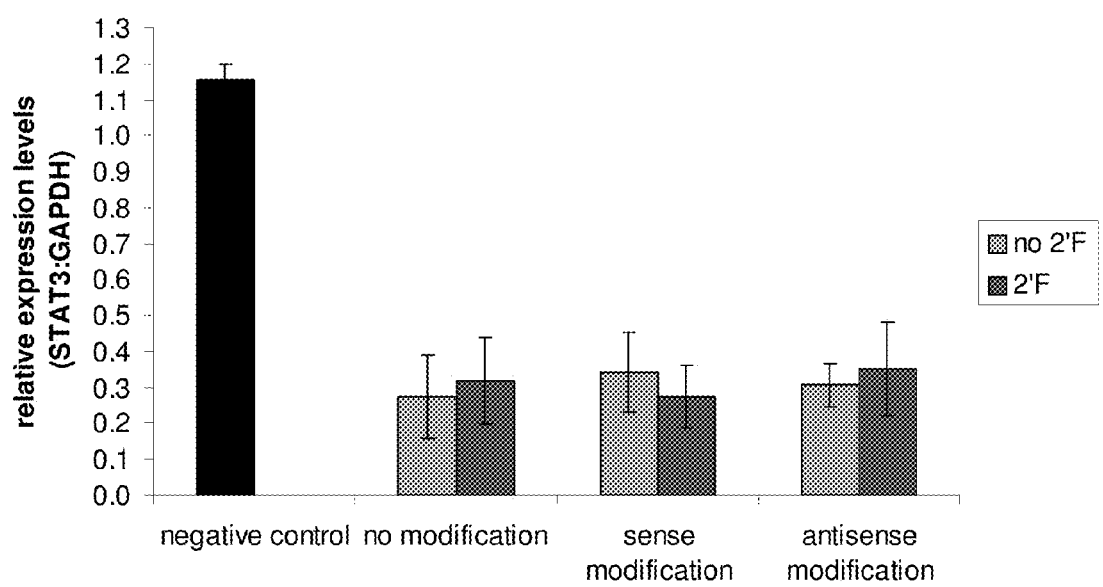
FIG. 22 is a bar graph illustrating the influence of 2'FC and 2'FU incorporation on the STAT3 knockdown efficiency of 5'-modified STAT3 siRNAs (sense modification and antisense modification) as compared to no modification.

In order to successfully knock down STAT3 expression in vivo the mAb-STAT3 siRNA conjugate has to be stable in human plasma. Since siRNAs with 2'F containing siRNA have been shown to be more stable in human plasma than unmodified siRNAs we evaluated whether the incorporation of 2'FU and 2'FC in the sense strand affects the knockdown efficiency. The knockdown efficiencies of AD and CH (no 5' modification, with and without 2'F incorporation), ED and GD (5' sense strand modified siRNAs with and without 2'F incorporation), AH and CD (5' antisense modified siRNAs with and with 2'F incorporation) were compared. As shown in FIG. 22, 2'FU/2'FC did not change the knockdown efficiency.

Influence of Various Linkers on the Knockdown Efficiency

To determine whether to use a cleavable or a non-cleavable linker for the Lewis-Y mAb-STAT3 siRNA conjugate, each of the modifiers in Table 6 were evaluated for their influence on knockdown efficiency.

TABLE 6

Modifiers to test for use of cleavable or non-cleavable linker.

| Modifier | Structure |
|---|---|
| Amino modifier | H$_2$N—(CH$_2$)$_6$—O—P(O$^-$)(=O)—O—(CH$_2$)$_3$—O—P(O$^-$)(=O)—O— siRNA-3' |
| Modifier 1 | 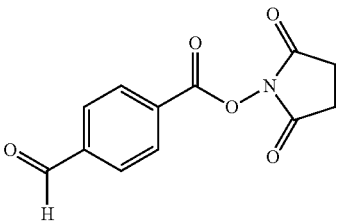 |

Modifier 1

TABLE 6-continued

Modifiers to test for use of cleavable or non-cleavable linker.

| Modifier | Structure |
| --- | --- |
| Modifier 2 | 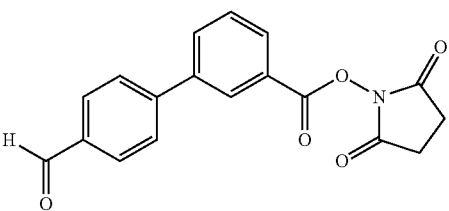<br>Modifier 2 |
| Modifier SS | 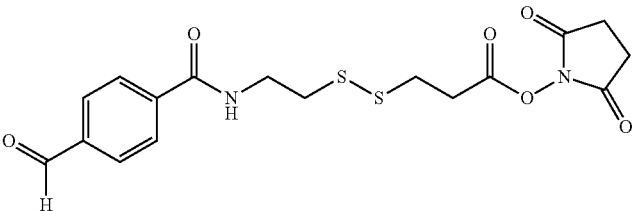<br>S-SS-4FB<br>Modifier SS |

Figure 23:
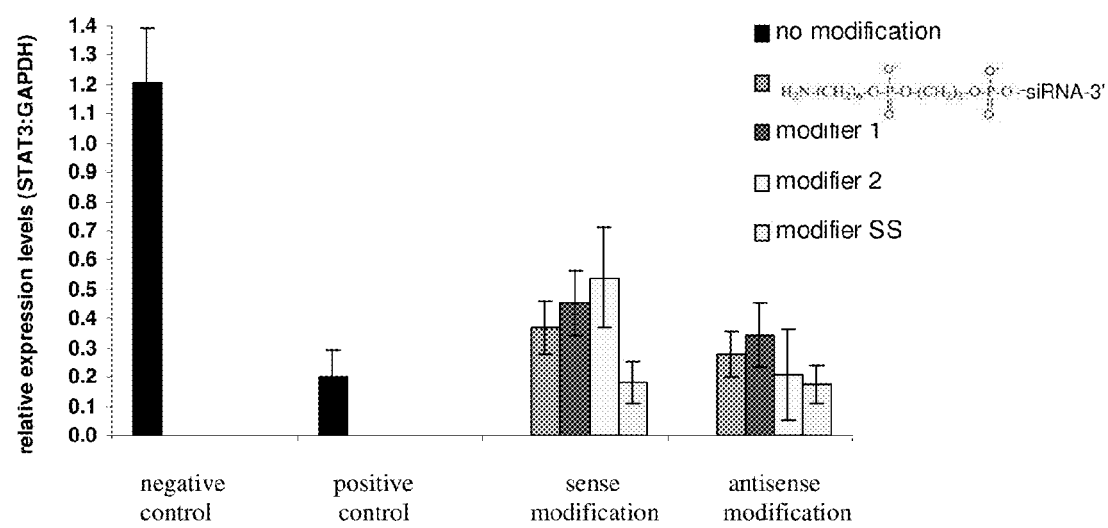
FIG. 23 is a bar graph illustrating the influence of cleavable and non-cleavable linkers on the STAT3 knockdown efficiency of 5'-modified STAT3 siRNAs (sense modification and antisense modification) as compared to no modification.

As shown in FIG. 23, the cleavable modifier SS did not affect the knockdown efficiency when attached to the 5' end of either the sense or antisense strand. The non-cleavable modifier 2 decreased the knockdown efficiency when attached to the 5' end of the sense strand. The attachment of modifier 2 to the 5' end of the antisense strand did not affect the knockdown efficiency. The results suggest that the siRNA should be attached to the 5' antisense strand if a non-cleavable linker is used to couple the siRNA to the mAb.

EXAMPLE 3

Knockdown Efficiency of hu3s193-siSTAT3 Conjugate

Because Modifier SS did not affect the STAT3 knockdown efficiency (FIG. 23) it was selected for conjugation of the Lewis-Y mAb (hu3S193) to the STAT3 siRNA (siSTAT3). The modifier was attached to the 5' end of the antisense strand. To evaluate the knockdown efficiency of the conjugate, STAT3 expression levels of DU-145 cells treated with the conjugate was compared to transfected with unmodified (AD) or 5' antisense SS-modified STAT3 siRNA. Two batches of mAb-STAT3 siRNA were initially tested: (1) conjugates with an antibody to siRNA ratio of 1:1 and (2) conjugates with an antibody to siRNA ratio of 1:2.

Figure 24:
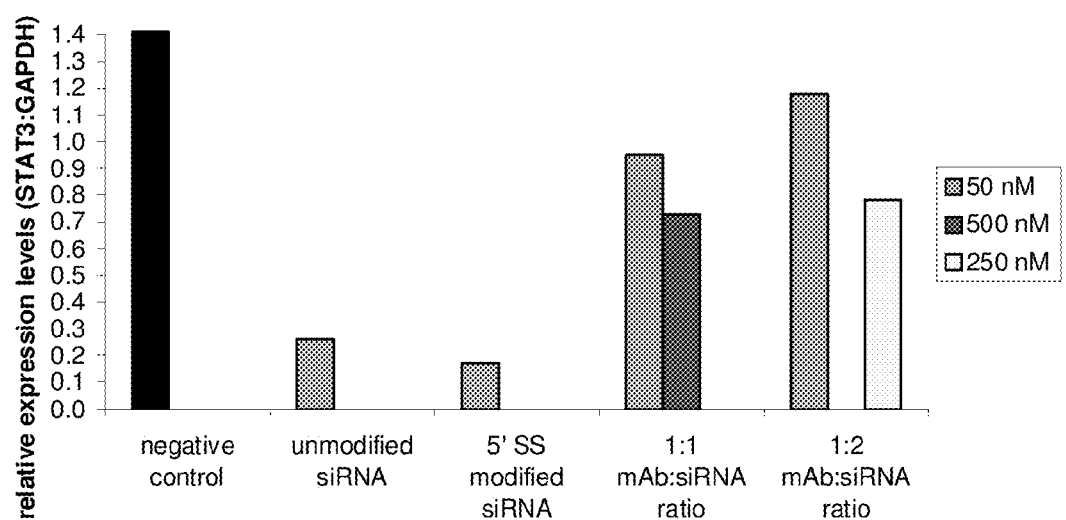
FIG. 24 is a bar graph illustrating the knockdown efficiencies of mAb-STAT3 siRNA conjugates and transfected siRNAs in DU-145 cells at various ratios and at various concentrations as shown.

The cells were treated with conjugate concentrations of 50 nM (1:1 and 1:2 mAb to siRNA ratios), 500 nM (1:1 mAb to siRNA ratio) and 250 nM (1:2 mAb to siRNA ratio, limited amount available). As shown in FIG. 24, STAT3 expression levels were not decreased in DU-145 cells when treated with the mAb-siRNA conjugates. The experiment was repeated using a fresh batch of mAb-STAT3 siRNA. After treatment with a conjugate concentration of 50 nM, 100 nM, 200 nM or 500 nM STAT3 expression levels were not significantly decreased (data not shown).

Figure 25:
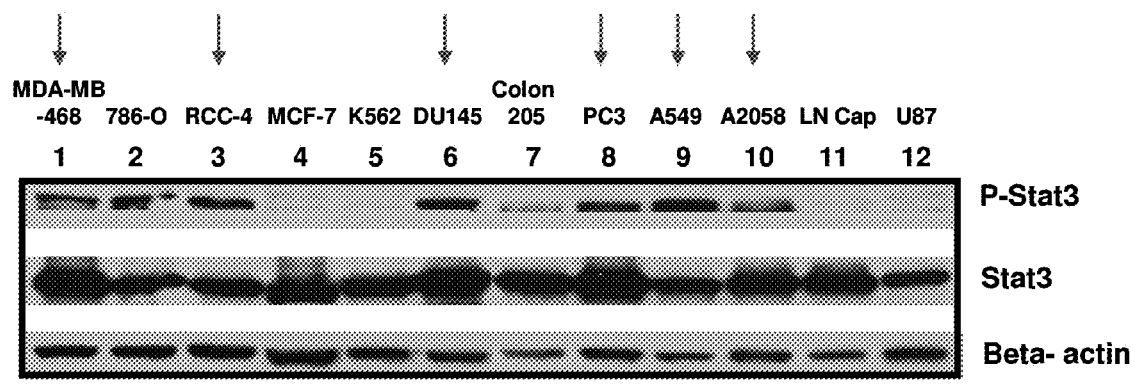
FIG. 25 is a Western analysis of pSTAT3 expression in various cell lines as shown.
Figure 26:
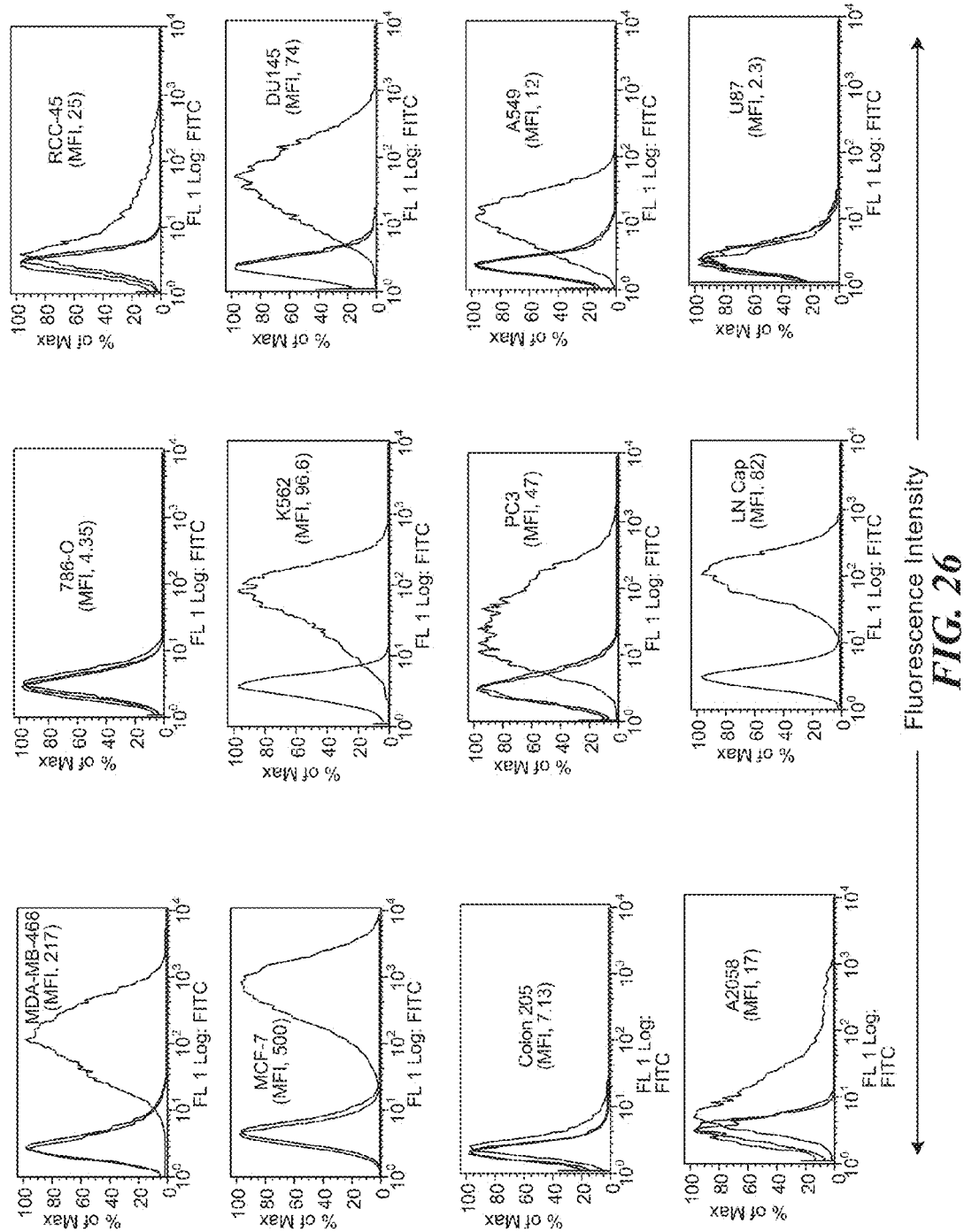
FIG. 26 is a series of FACS analysis results of $Le^Y$ expression on various cell lines.

In addition to DU145, twelve other cell lines were examined for $Le^Y$ positivity and STAT3 expression for future use. These results are presented in FIGS. 25 and 26, respectively.

Figure 34:
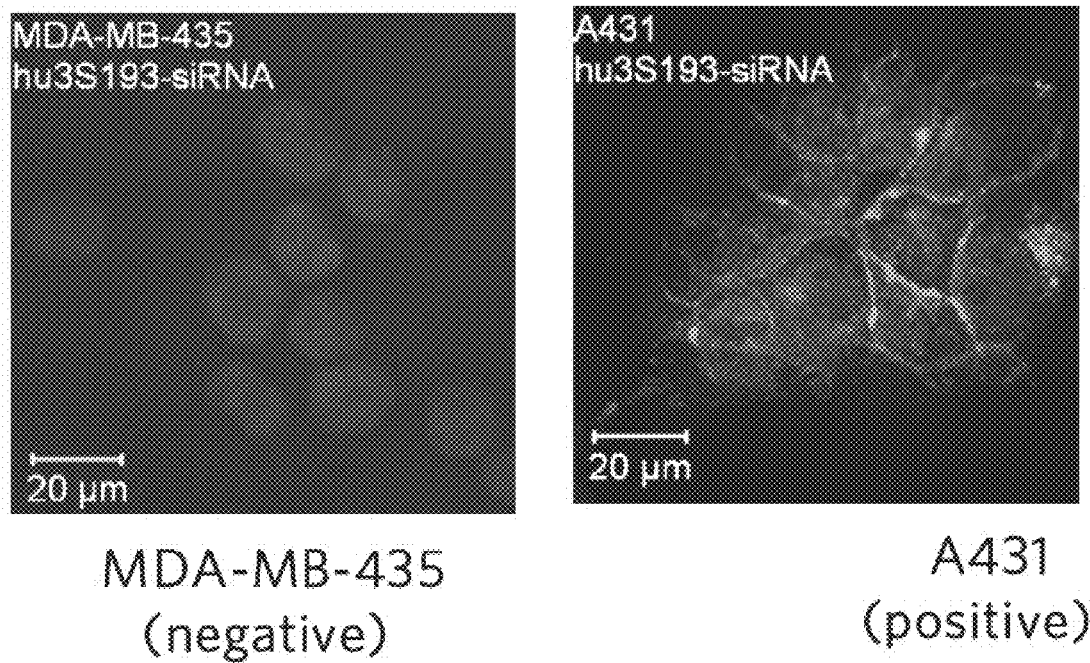
FIG. 34 are representative images of a confocal analysis using fluorescence labeled siRNA illustrating that the mAb-siRNA construct (hu3S193-siRNA) is internalized by $Le^Y$ positive (A431) cells but are not internalized by $Le^Y$ negative (MDA-MB-435) cells.
Figure 35:
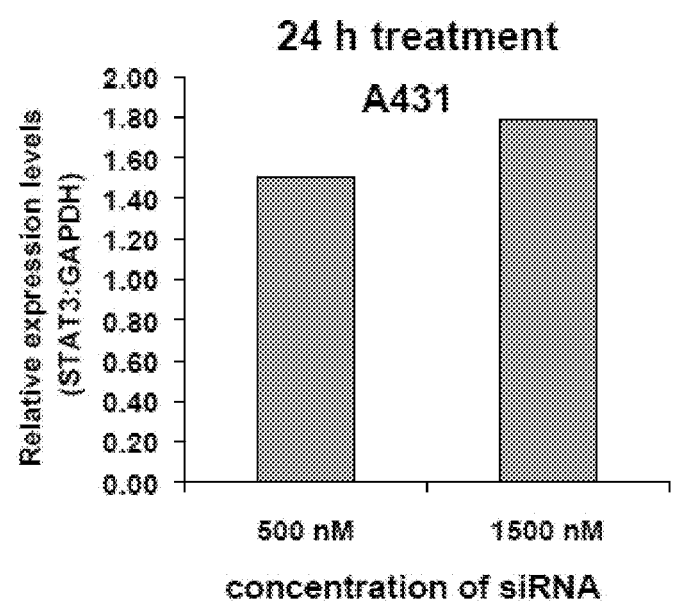
FIG. 35 shows the knockdown efficiency of the mAb-siRNA construct (hu3S193-siRNA) in $Le^Y$ positive A431 cell line.

In addition to DU145 prostate tumor cells (purchased from ATCC) which contain both high levels of activated STAT3 (p-Stat3) and Lewis Y, MDA-MB-468 breast cancer line is also highly positive for both markers. There are several other tumor cell lines that are positive for both, to varying extents. These include: RCC-4, PC3, A2058, and A549. Using available cell lines, the knockdown efficiency of the hu3S193-siSTAT3 conjugate was determined for available $Le^Y$ positive and $Le^Y$ negative cell lines No significant knockdown was observed in A431 cells (FIG. 35). Internalization was observed using fluorescently labeled (FITC) conjugates by confocal microscopy in a cell line that expresses $Le^Y$ antigen ($Le^Y$ positive; A431) but not in a cell line that does not express $Le^Y$ antigen ($Le^Y$ negative; MDA-MB-435) (FIG. 34).

Figure 36:
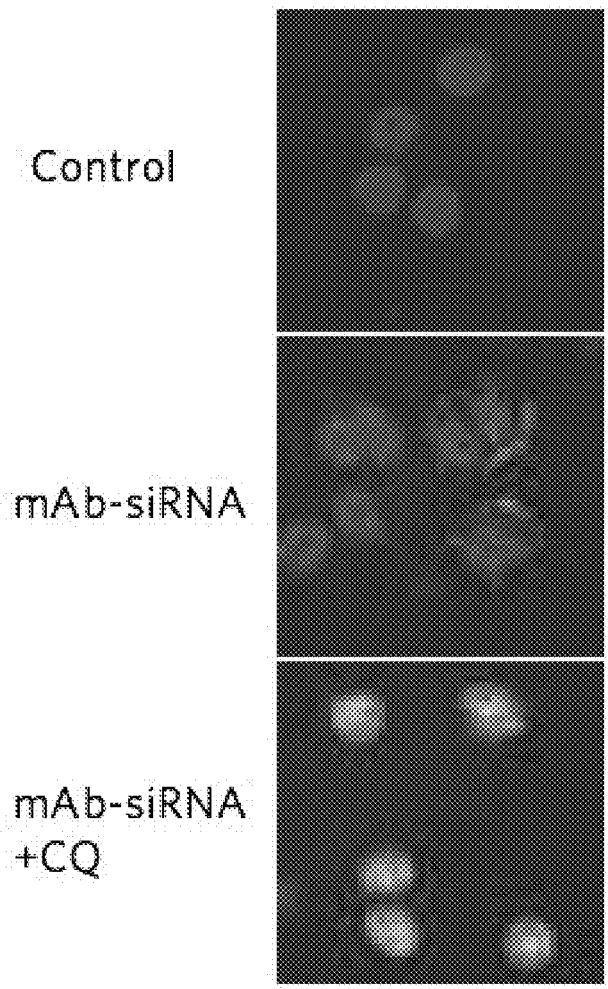
FIG. 36 are representative images of a confocal analysis using fluorescence labeled siRNA illustrating that the mAb-siRNA construct (hu3S193-siRNA) is internalized by $Le^Y$ positive (mAb-siRNA), but not internalized by $Le^Y$ negative cells (control) and the addition of chloroquine (CQ), an endosomal disrupting agent, allows uniform siRNA distribution within cells (mAb-siRNA+CQ).

Since the mAb-siRNA conjugate is internalized by the $Le^Y$ positive cells but did not affect the knockdown efficiency, it is likely trapped in the endosome, preventing it from reaching the target RNA in the cell. An endosome disrupting reagent, chloroquine (CQ) can provide uniform siRNA distribution within cells, which confirms that the problem was endosome trapping of the delivery vehicle (FIG. 36).

Figure 37:
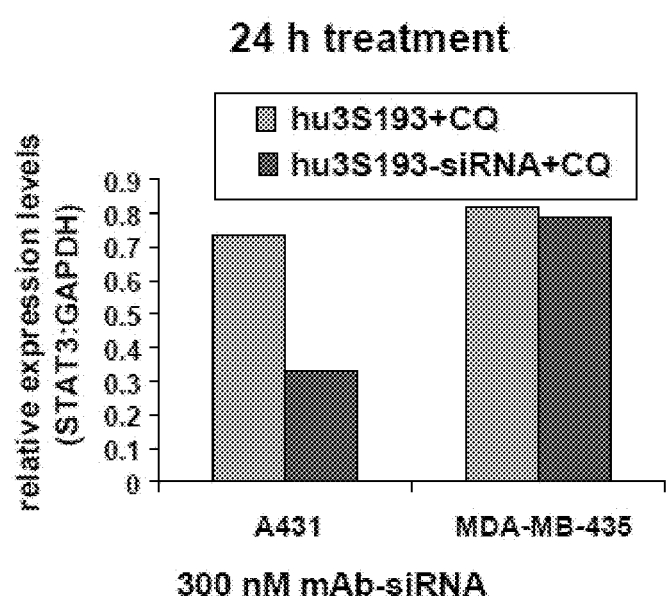
FIG. 37 shows the knockdown efficiency of the mAb-siRNA construct (hu3S193-siRNA) with CQ in $Le^Y$ positive (A431) and $Le^Y$ negative (MDA-MB-435) cell lines.

A significant improvement on knockdown efficiency was achieved with the facilitate of CQ in antigen highly expressed cell lines (A431) but not a cell line that does not express $Le^Y$ (MDA-MB-435) showing the selective delivery and gene knockdown (FIG. 37).

Figure 38:
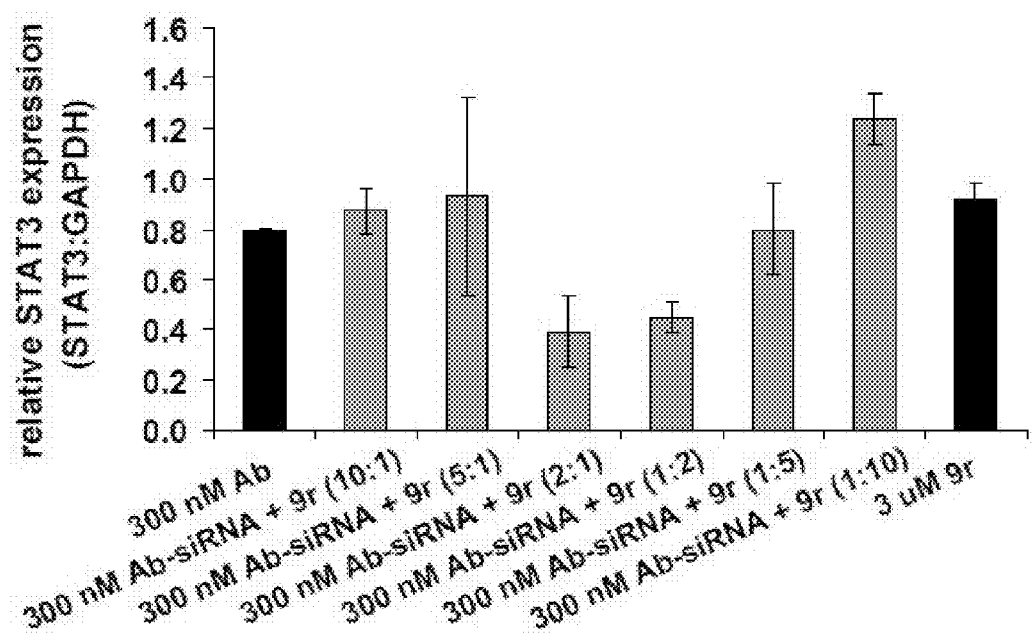
FIG. 38 shows the knockdown efficiency of the mAb-siRNA construct (hu3S193-siRNA) with and without the addition of (D-Arg)$_9$ (9R).

Knockdown efficiency was also improved with 9R. Arginine (Arg) peptide has been used for siRNA delivery, and D-Arg peptide has been used due to higher stability. Co-treatment with 9R increased knockdown efficiency of mAb-siRNA covalent construct (FIG. 38). Knockdown was only observed with antigen high expression cell lines.

Other methods for improving knockdown efficiency may include the use of different linkers and linker lengths to optimize knockdown efficiency.

EXAMPLE 4

Generation of Noncovalently Conjugated Monoclonal Antibody-siRNA Complexes

Figure 39:
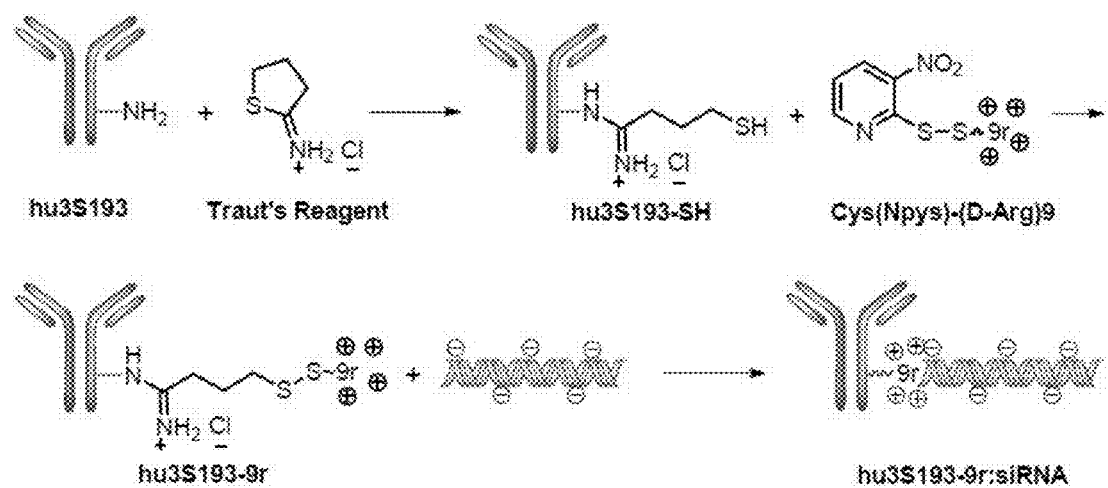
FIG. 39 illustrates the synthesis of a non-covalent mAb-siRNA construct (hu3S193-9R:siRNA).
Figure 40:
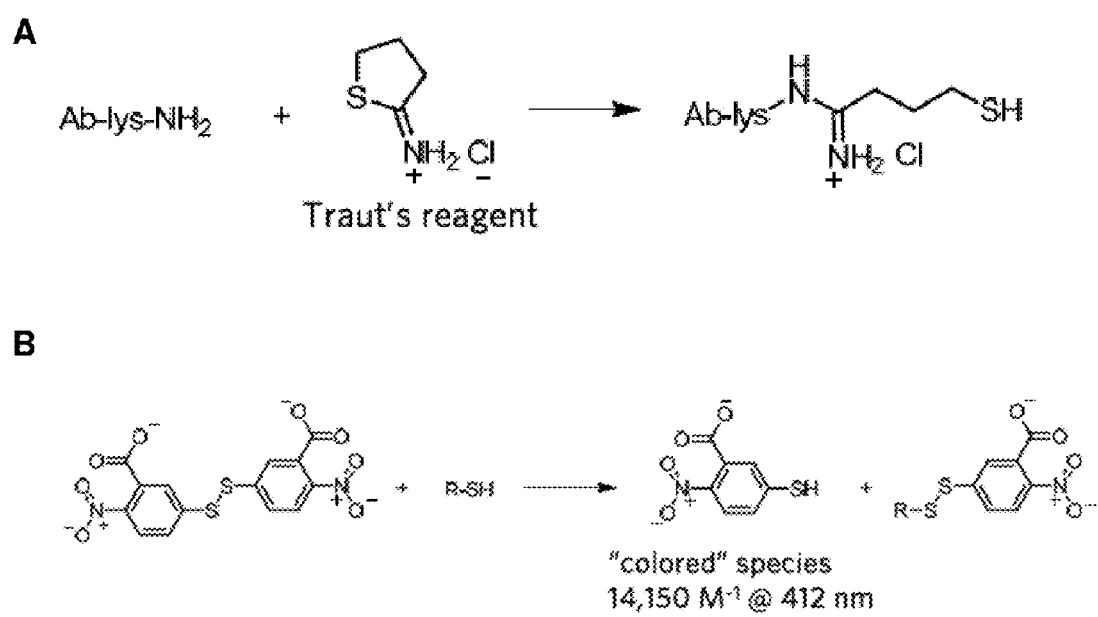
FIG. 40 illustrates the quantification of the hu3S193-linker construct. Modification (A) was completed under the following reaction conditions: hu3S193 (10 mg/ml), 100 mM phosphate, 150 mM NaCl and 10 mM EDTA, pH 7.5, 10 eq, Traut's reagent at 22° C. for 1 hour. Quantification of the —SH group on the Antibody after modification by Ellman's Reagent yielded a "colored" species.

An alternative strategy based on 9R was developed for comparison with covalently conjugated mAb-siRNA complexes such as those described above. Instead of direct or covalently linking siRNA to mAb, the mAb may be modified with a positively charged peptide (e.g., 9R) such that negatively charged siRNA may be delivered by exploiting electrostatic interactions between the siRNA and 9R peptide. To accomplish this non-covalent conjugation, hu3S193 was thiolated using Traut's reagent then allowed to react with (Npys) Cys-9-D-Arg. The positively charged mAb-9R construct can associate with negatively charged siRNA for delivery (FIG. 39). Modification and Quantification of the hu3S193-linker construct is shown in FIG. 40.

Figure 41:
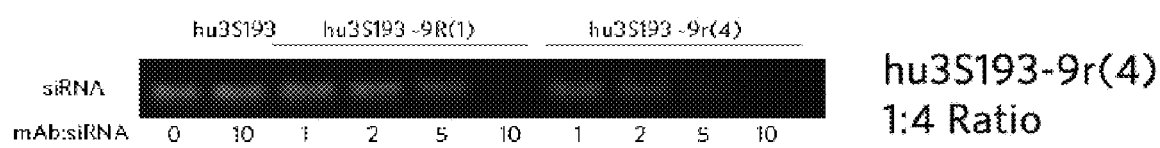
FIG. 41 illustrates siRNA binding with huS193-9r(1) and huS193-9r(4) using electronic gel mobility-shift assay (EMSA)

Hu3S193-9R Binds to siRNA. Efficient siRNA binding to hu3S193-9R (9R:hu3S193=1.2) at a mAr-9R:siRNA ratio of 10:1 was confirmed by electrophoretic gel mobility-sift assay (FIG. 41).

Figure 42:
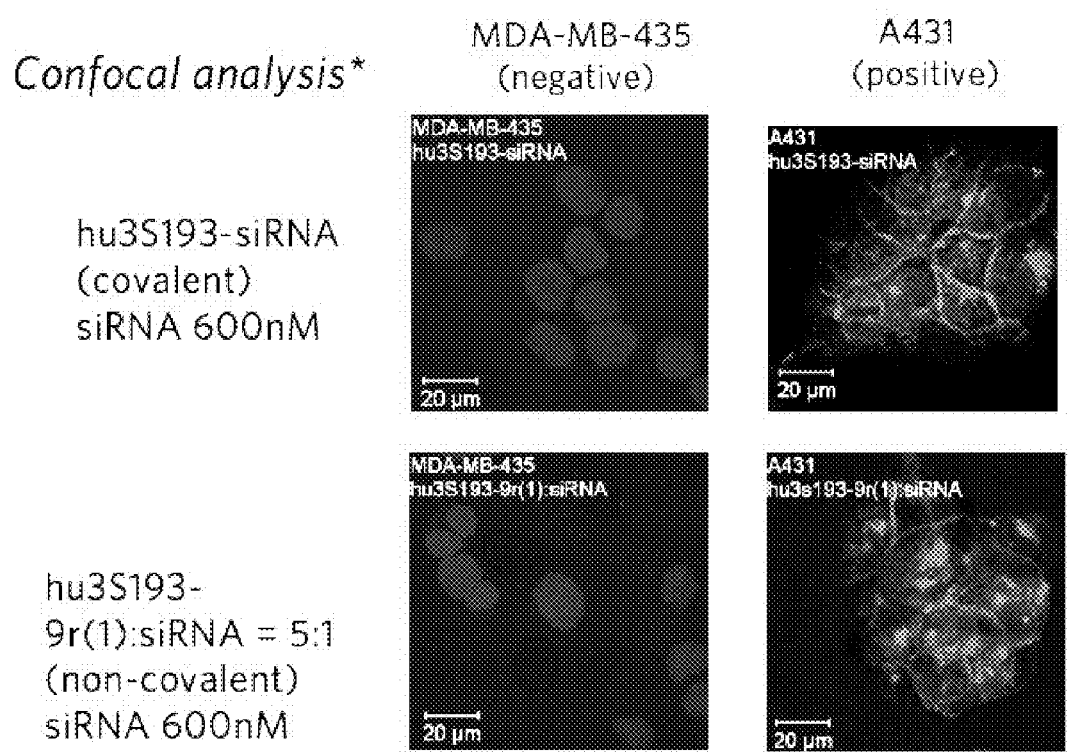
FIG. 42 is a set of images illustrating the results of a confocal analysis showing that covalent and non-covalent hu3S193 and siRNA conjugates are internalized by Le$^{Y+}$ cells (A431) but not by Le$^{Y-}$ cells (MDA-MB-435).
Figure 47:
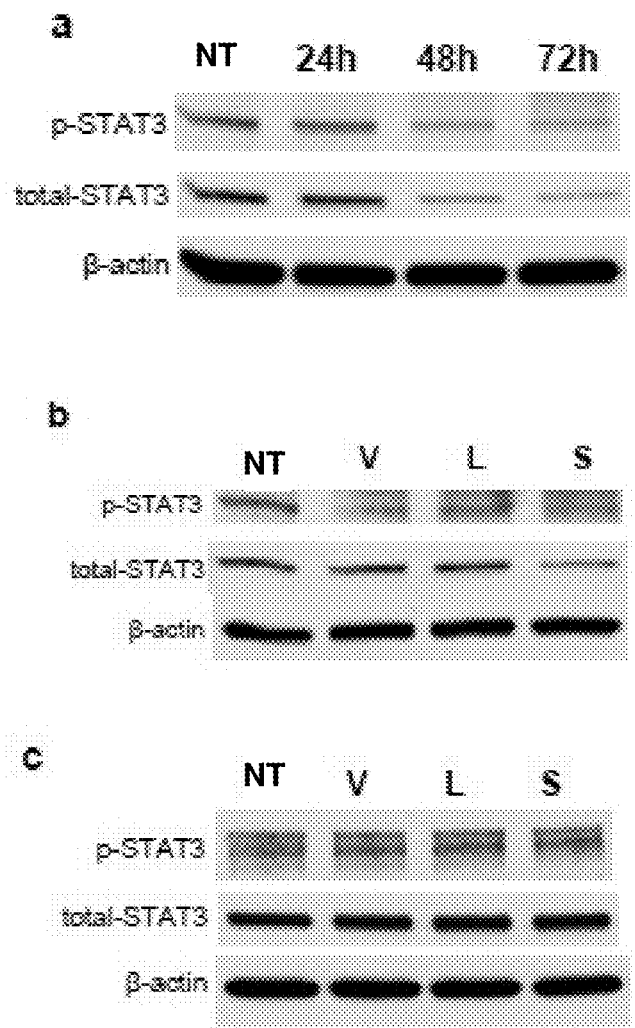
FIG. 47 shows a set of Western Blots illustrating the effect of hu3S193-9R(1):siRNA=5:1 on the expression of STAT3 upon administration to Le$^{Y+}$ (A431) or Le$^{Y-}$ (MDA-MB-435) cells. (A) Shows the expression of pSTAT3, total-STAT3 and β-actin (housekeeping) in A431 cells after no treatment (NT or treatment with hu3S193-9R(1):siSTAT3=5:1 at 24, 48 and 72 hours. (B) and (C) show expression of pSTAT3, total-STAT3 and β-actin (housekeeping) in A431 cells (B) and MDA-MB-435 cells (C) after no treatment (NT), treatment with hu3S193-9R(1) alone (V) for 72 hours, treatment with hu3S193-9R(1):siLuci=5:1 (L; control) for 72 hours, or treatment with hu3S193-9R(1):siSTAT3=5:1 (S) for 72 hours.

Hu3S193-9R specifically delivers siRNA. As determined by FACS analysis, the mAb-9R construct was able to transduce siRNA into antigen expression cells (A431, MDA-MB-468) but not antigen negative cells (MDA-MB-435) (See Table 7 below). Similar results were indicated by confocal image (FIG. 42). This is corroborated by suppression of STAT3 protein expression after treatment for 72 hours with the mAb-9R construct as shown by Western Blot (FIG. 47).

TABLE 7

Flow cytometry results indicate that mAb-9R was able to transduce siRNA into antigen expression cells (A431, MDA-MB-468) but not antigen negative cells (MDA-MB-435).

|  | MDA-MB-435 ($Le^{Y-}$) | DU145 ($Lev^{Y+}$) | MDA-MB-468 ($Le^{Y+}$) | A431 ($Le^{Y+}$) |
| --- | --- | --- | --- | --- |
| hu3S193-FAM | <1% | 53% | >99% | >99% |
| siRNA-FAM | <1% | <1% | <1% | <1% |
| hu3S193-9R:siRNA-FAM (non-covalent) | <1% | 24% | 57% | 98% |

Figure 43:
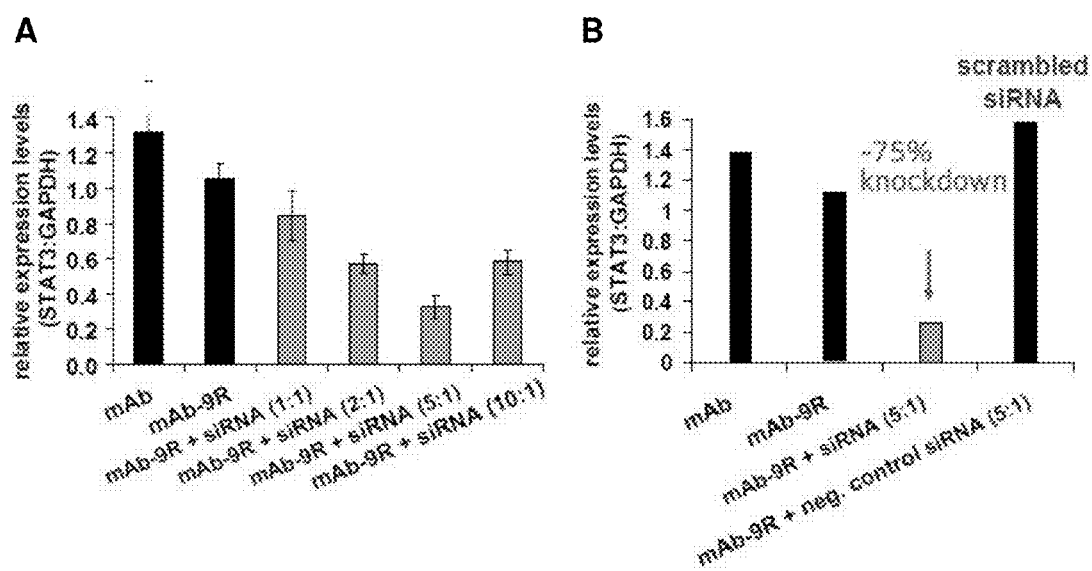
FIG. 43 are bar graphs illustrating that the optimum molar ratio of non-covalent hu3S193-9R(1):siRNA is 5:1 (A) and that the 5:1 molar ratio showed a ~75% knockdown efficiency (B).

Optimum molar ratio for knockdown efficiency. Knockdown of STAT3 was determined using various ratios (1:1, 2:1, 5:1 and 10:1) of hu3S193-9R(1):siRNA. As shown in FIG. 43A, the optimum molar ratio was 5:1 (hu3S193-9R(1):siRNA(5:1)). FIG. 43B shows that administration of hu3S193-9R(1):siRNA(5:1) resulted in approximately 75% knockdown compared to controls.

Figure 45:
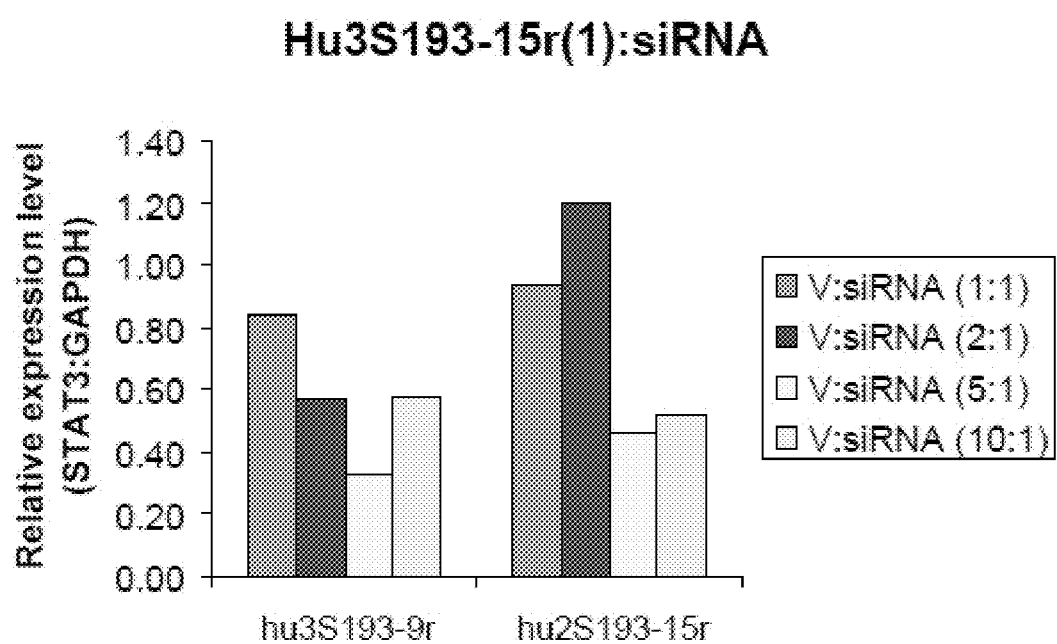
FIG. 45 is a bar graph illustrating the knockdown efficiency of (Arg)$_9$ (9R) peptide modification in hu3S193-9R(1):siRNA compared to that of (Arg)$_{15}$ (15R) peptide modification in a'hu3S193-15r(1):siRNA construct.

Although other positively charged Arginine peptides may be used to generate non-covalent antibody-siRNA complexes, increasing the number of positively charged residues in such peptides (e.g., 15R) does not appear to improve knockdown efficiency of the complexes (FIG. 45).

The ratio of hu3S193 to 9R affects the specificity of the antibody-siRNA complex or conjugate's binding to target cells as determined by FACS analysis. As shown in Table 8 below, a hu3S193 to 9R ratio of 1:1 (hu3S193-9r(1)) shows specific binding to $Le^Y$ positive cells, whereas a hu3S193 to 9R ratio of 1:4 (hu3S193-9r(4)) shows significant nonspecific binding.

TABLE 8

Specific Binding to Target Cells- results of FACS analysis (Fluorescence labeled siRNA was used for FACS)

|  | MDA-MB-435 ($Le^{Y-}$) | A431 ($Le^{Y+}$) |
| --- | --- | --- |
| $Le^Y$ expression | 4% | 98% |
| siRNA alone - | 1% | 1% |
| hu3S193-siRNA (covalent) | 4% | 67% |
| hu3S193-9R(1):siRNA = 1:1 (non-covalent) | n.d. | 98% |
| hu3S193-9R(1):siRNA = 2:1 (non-covalent) | n.d. | 98% |
| hu3S193-9R(1):siRNA = 5:1 (non-covalent) | 1% | 98% |
| hu3S193-9R(4):siRNA = 1:1 (non-covalent) | 1% | 97% |
| hu3S193-9R(4):siRNA = 2:1 (non-covalent) | 43% | 97% |
| hu3S193-9R(4):siRNA = 5:1 (non-covalent) | 97% | 98% |
| hu3S193-9R:siRNA-FAM (non-covalent) | <1% | 98% |

Figure 44:
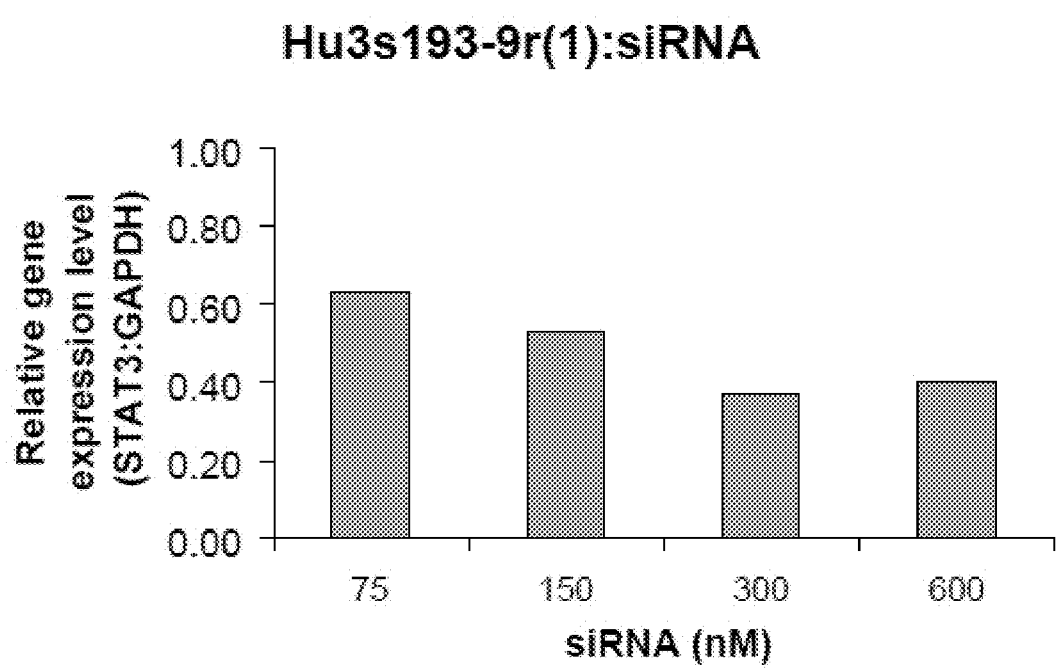
FIG. 44 is a bar graph illustrating the knockdown efficiency using various concentrations of siRNA.

Further, as shown in FIG. 44, the optimal concentration of siRNA used in a hu3S193-9r(1):siRNA construct is 300 nM.

Figure 46:
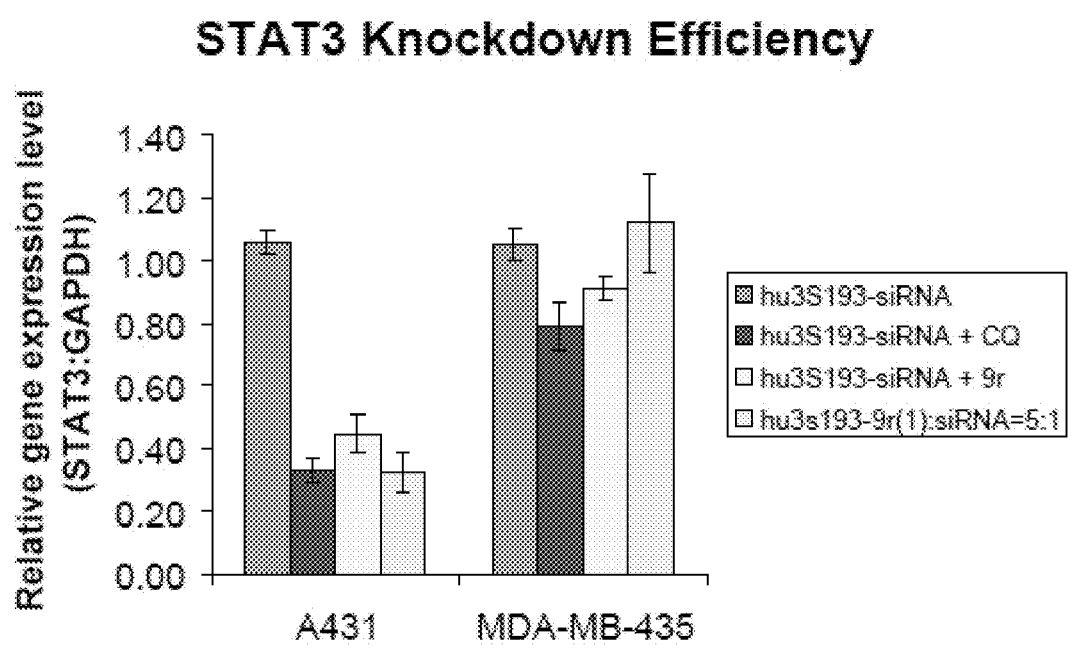
FIG. 46 is a bar graph illustrating STAT3 knockdown efficiency of covalent (hu3s193-siRNA alone, with CQ or with 9R) and non-covalent (hu3S193-9R(1):siRNA=5:1) conjugates in A431 cells as compared to in MDA-MB-435 cells.
Figure 49:
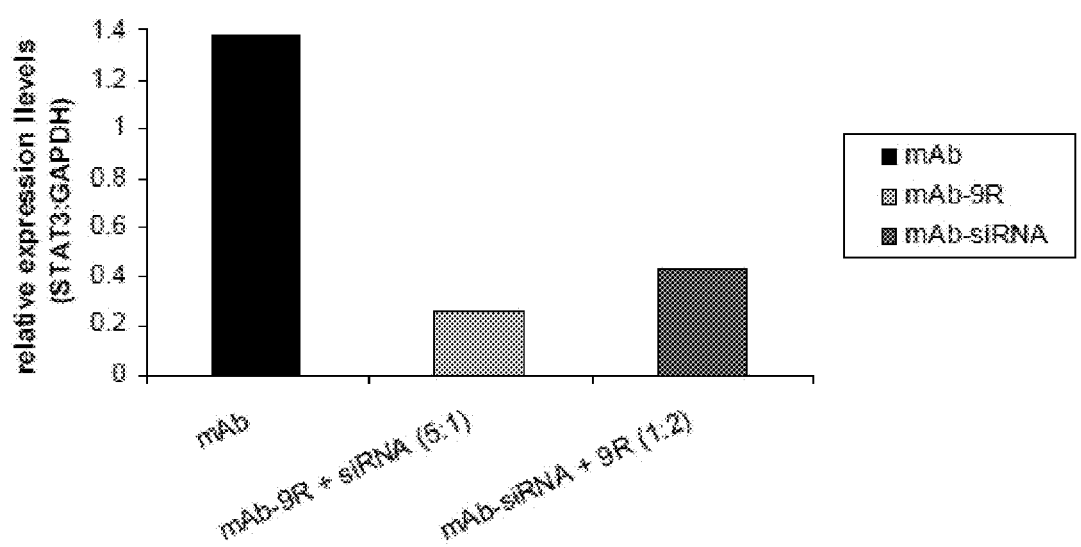
FIG. 49 is a bar graph comparing the knockdown efficiency of covalent (mAn-9R+siRNA (5:1)) and non-covalent (mAb-siRNA+9R (1:2)) complexes in A431 cells.

Comparison of Non-covalently Conjugated Complexes to Covalently Conjugated Complexes The non-covalent system hu3S193-9R(1.2)/siRNA complex and covalent system hu3S193-siRNA:9R show similar knockdown efficiency in a A431 cell line. The non-covalent system has higher knockdown efficiency compared to the covalent system (FIGS. 46 and 49).

Cell Proliferation Assay

Figure 48A:
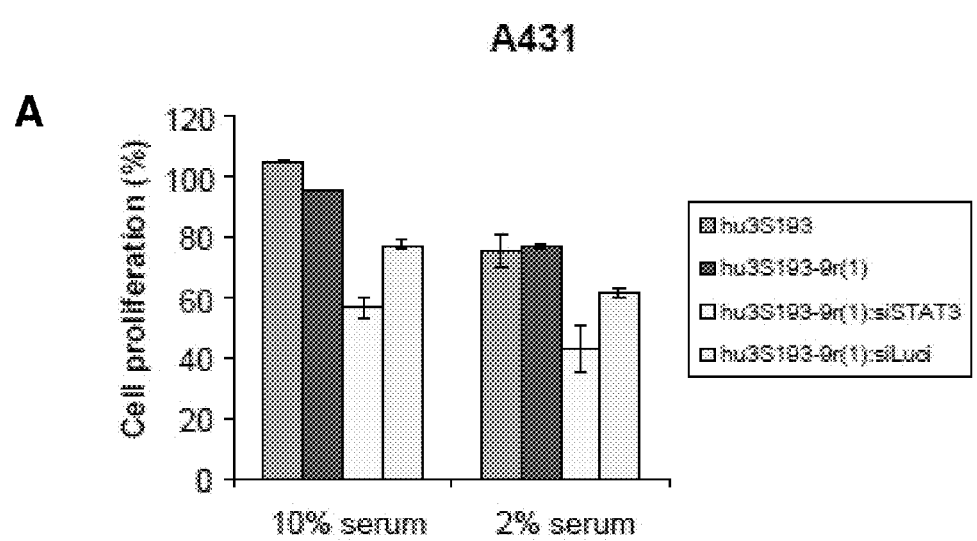
FIG. 48 are bar graphs illustrating the effects of hu3S193 (alone), hu3S193-9R(1) (alone), hu3S193-9R(1):siSTAT3 and hu3S193-9R(1):siLuci on cell proliferation in Le$^{Y+}$ (A431) (A) and Le$^{Y-}$ (MDA-MB-435) (B) cells.
Figure 48B:
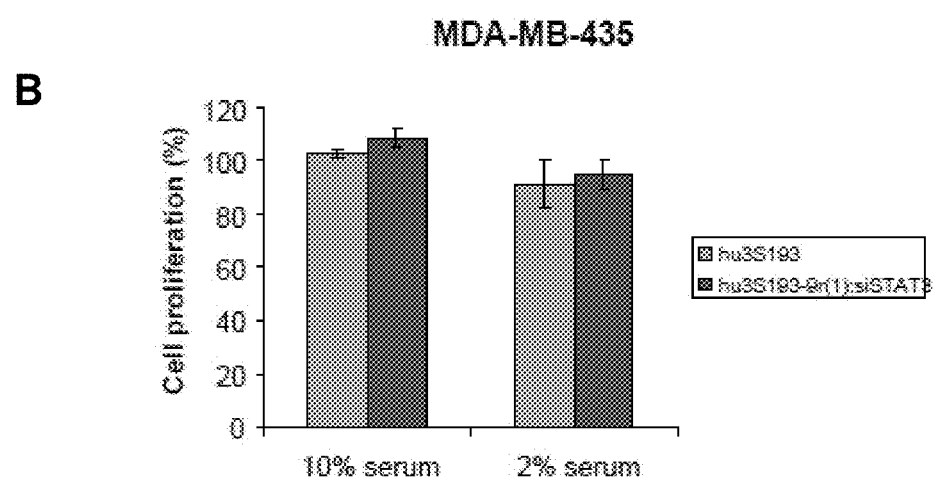

To determine if the non-covalent mAb-9R construct's ability to knockdown STAT3 expression results in suppressing proliferation in $Le^{Y+}$ cancer cells, a cell proliferation assay was performed (FIG. 48). The mAb-9R construct (hu3S193-9r(1):siSTAT3) caused a decrease in cell proliferation in A431 cells ($Le^{Y+}$) (FIG. 48(A)), but not in MDA-MB-435 cells ($Le^{Y-}$) (FIG. 48(B)). These results suggest that the hu3S193-9r(1):siSTAT3 conjugate may be used in the treatment of cancer to suppress tumor cell proliferation, thereby preventing, reducing or suppressing primary tumor growth and metastasis.

REFERENCES

The references cited in the specification above and those listed below are hereby incorporated by reference as if fully set forth herein.

Aigner A: Applications of RNA interference: current state and prospects for siRNAbased strategies in vivo. Appl Micro Biotechnol2007, 76: 9-21.

Boghaert E R, Sridharan L, Armellino D C, Khandke K M, DiJoseph J F, Kunz A, Dougher M M, Jiang F, Kalyandrug L B, Hamann P R, Frost P, Damle N K. Antibody-Targeted Chemotherapy with the Calicheamicin Conjugate hu3S193-N-Acetyl γ Calicheamicin Dimethyl Hydrazide Targets Lewis$^y$ and Eliminates Lewis$^y$-Positive Human Carcinoma Cells and Xenografts Clinical Cancer Research 2004, 10, 4538-4549.

Daniel M C, Astruc D: Gold nanoparticles: assembly, supramolecular chemistry, quantum-size-related properties, and applications toward biology, catalysis, and nanotechnology. Chern Rev 2004, 104: 293-346.

Gingrich J R. Barrios R J, Morton R A, Boyce B F, DeMayo F J, Finegold M J, Angelopoulou R, Rosen J M: Metastatic prostate cancer in a transgenic mouse. Cancer Res, 1996, 56:4096-4102.

Greenberg N M, DeMayo F, Finegold M J, Medina D, Tilley W D, Aspinall J O, Cunha G R, Donjacour A A, Matusik R J, Rosen J M: Prostate cancer in a transgenic mouse. Proc Natl Acad Sci USA, 1995, 92:3439-3443.

Kumar S, Harrison N, RichardS-Kortum, R, Sokolov K: Plasmonic nanosencors for imaging intracellular biomarkers in live cells. Nano lett, 2007, 7(5): 1338-1343.

Li I, Yazaki P J, Anderson A I, Crow D, Colcher D, Wu A M, Williams I E, Wong J Y C, Raubitschek A, Shively J E: Improved biodistribution and radioimmunoimaging with poly(ethyleneglycol)-DOTA-conjugated anti-CEA diabody. Bioconjugate Chern, 2006, 17:68-76.

Liu H, Moy P, Xia Y, Kim S, Rajasekaran A K, Navarro V, Knudsen B, Bander N H: Monoclonal antibodies to the extracellular domain of prostate-specific membrane antigen also react with tumor vascular endothelium. Cancer Res, 1997, 57:3629-3634.

Matt O M, Nuutinen U M, Hakkarainen T, Tallone T, Wahlfor J, Peikonen J: hCAR-EGFP fusion receptor in human follicular lymphoma B cells—A model for adenoviral gene therapy for B cell malignancies. Int. Mol Med 2006, 17: 1057-1062.

Mukherjee P, Bhattacharya R, Bone N, lee YK, Patra C R, Wang S, lu I, Secreto C, Banerjee P C, Yaszemski M J, Kay N E, Mukhopadhyay D: Potential therapeutic application of gold nanoparticles in B-chronic lymphocytic leukemia (BCH): enhancing apoptosis. J Nanobiotechnology 2007, 5:4 doi: 10.1186/1477-3155-5-4.

Nakagawa K, Noguchi Y, Uenaka A, Sato S, Okumura H, Tanaka M, Shimono M, Eldib A M A, Ono T, Ohara N, Yoshino T, Yamashita K, Tsunoda T, Aoe M, Shimizu N, Nakayama E: XAGE-1 expression in non-small cell lung cancer and antibody response in patients. Clin Cancer Res, 2004, 11 (15): 5496.

Paciotti G F, Myer I, Weinreich D, Pavel R, Mclaughlin R E, Tamarkin I: Colloidal gold: a novel nanoparticle vector for tumor directed drug delivery. Drug Deliv 2004, 11:169-183.

Qu Z X, Goldenberg O M, Cardillo T M, Shi V, Hansen H J, Chang C H: Bispecific antiCD20/22 antibodies inhibit B-cell lymphoma proliferation by a unique mechamism of action. Blood, 2007: D0110.11821 blood-2007-08-110072.

Rosi N I, Giljhann D A, Thazton C S, lytton-Jean, AKR, Han M S, Mirkin C A: Oligonucleotide-modified gold nanoparticles for intracellular gene regulation. Science, 2006, 312: 1027-1030.

Scott A M, Tebbutt N; Lee F T, Cavicchiolo T, Liu Z, Gill S, Poon A, Hopkins W, Smyth F E, Murone C, MacGregor O, Papenfuss A, Chappell B, Saunder T, Johns T G, Brechbiel M W, Davis 10, Murphy R, Chong G, Stockert E, Ritter G, Hoffman E W, Old I J: Phase I trial of humanized monoclonal antibody hu3S193 in patients with advance epithelial cancers which express the lewis-y antigen. Clin Cancer Res, 2007, 13(11):3286-3292.

Silver D A, Pellicer I, Fair W R, Heston W D W, Cordon-Cardo C: Prostate-specific membrane antigen expression in normal and malignant human tissues. Clin Cancer Res, 1997, 3:81-85.

Simpson A J G, Caballero O L, Jungbluth A, Chen Y T, Old I J: Cancer/testis antigens, gametogenesis and cancer. Nature Reviews Cancer, 2005, 5, 615.

Smith M R: Rituximab (monoclonal anti-CD20 antibody): mechanism of action and resistance. Oncogene 2003, 22: 7359-7368.

Wang T, Niu G, Kortylewski M, Jove R, Yu H: Regulation of the innate and adaptive immune responses by 51al-3 signaling in tumor cells. Nature Medicine, 2004, 10:48-54.

Yu H, Jove R: The STATs of cancer—new molecular targets come of age. Nature Rev Cancer, 2004, 4:97-105.

Yu H, Kortylewski M; Pardoll D: Crosstalk between cancer and immune cells: Role of STAT3 in tumour microenvironment. Nature Rev Immunology, 2007, 7:41-51.

---

What is claimed is:

1. A method for covalently conjugating an antibody or functional fragment thereof with an siRNA molecule, the method comprising:
 modifying a Lewis Y (Le$^Y$) antibody or functional fragment thereof with a linker to provide a linker-modified Le$^Y$ antibody;
 combining a target siRNA against STAT3 (siRNA$_{STAT3}$) with a disulfide containing aldehyde linker to provide a linker-modified target siRNA$_{STAT3}$; and
 combining the linker-modified target siRNA$_{STAT3}$ with the linker-modified Le$^Y$ antibody to form a Le$^Y$ antibody-siRNA$_{STAT3}$ complex.

2. The method of claim 1, wherein the Le$^Y$ antibody is a hu3S193 antibody.

3. The method of claim 1, wherein the linker-modified Le$^Y$ antibody is modified with a 6-hydrazin onicotinamide (HyNic) linker.

4. The method of claim 1, wherein the disulfide containing aldehyde linker includes a phosphoramidite.

5. The method of claim 1, wherein the siRNA$_{STAT3}$ comprises a sense strand having the RNA sequence selected from the group consisting of:
 (S1): 5'-rGrGrA rArGrC rUrGrC rArGrA rArArG rArUrA rCrGrA rCrUdG dA-3' (SEQ ID NO: 1);
 (S2): 5'-rGrGrA rArGrC rUrGrC rArGrA rArArG rArUrA rCrGrA rCrUrG rA-3' (SEQ ID NO: 2); and
 (S3): 5'-rGrGrA rArGfC fUrGfC rArGrA rArArG rAfUrA fCrGrA fCfUdG rA-3' (SEQ ID NO: 3).

6. The method of claim 1, wherein the siRNA$_{STAT3}$ comprises an antisense strand having the RNA sequence of:
 (A1) 5'-rUrCrA rGrUrC rGrUrA rUrCrU rUrUrC rUrGrC rArGrC rUrUrC rCrGrU-3' (SEQ ID NO: 4).

7. The method of claim 1, wherein the Le$^Y$ antibody-siRNA$_{STAT3}$ complex is further conjugated to a nanoparticle.

8. The method of claim 7, wherein the nanoparticle is a gold nanoparticle (AuNP).

9. The method of claim 7, wherein the nanoparticle contains one or more drug molecules.

10. The method of claim 1, wherein the Le$^Y$ antibody-siRNA$_{STAT3}$ complex is further conjugated to a visualization agent.

11. The method of claim 10, wherein the visualization agent is selected from the group consisting of a radioisotope, radionuclide, radiolabel, radiotracer, dye, contrast agent, fluorescent compound, bioluminescent compound, and enhancing agent.

* * * * *

SEQUENCE LISTING

```
<160> NUMBER OF SEQ ID NOS: 28

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide: S1
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 1
ggaagcugca gaaagauacg acuga                                           25

<210> SEQ ID NO 2
<211> LENGTH: 25
<212> TYPE: RNA
<213> ORGANISM: Artificial Sequence
<220> FEATURE:
<223> OTHER INFORMATION: Synthetic oligonucleotide: S2

<400> SEQUENCE: 2
ggaagcugca gaaagauacg acuga                                           25
```

```
<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide; S3
<220> FEATURE:
<221> NAME/KEY: modified_base
<222> LOCATION: (6)..(6)
<223> OTHER INFORMATION: 2'-fluoro-C
<220> FEATURE:
<221> NAME/KEY: modified_base
<222> LOCATION: (7)..(7)
<223> OTHER INFORMATION: 2'-fluoro-U
<220> FEATURE:
<221> NAME/KEY: modified_base
<222> LOCATION: (9)..(9)
<223> OTHER INFORMATION: 2'-fluoro-C
<220> FEATURE:
<221> NAME/KEY: modified_base
<222> LOCATION: (17)..(17)
<223> OTHER INFORMATION: 2'-fluoro-U
<220> FEATURE:
<221> NAME/KEY: modified_base
<222> LOCATION: (19)..(19)
<223> OTHER INFORMATION: 2'-fluoro-C
<220> FEATURE:
<221> NAME/KEY: modified_base
<222> LOCATION: (22)..(22)
<223> OTHER INFORMATION: 2'-fluoro-C
<220> FEATURE:
<221> NAME/KEY: modified_base
<222> LOCATION: (23)..(23)
<223> OTHER INFORMATION: 2'-fluoro-U
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 3
ggaagcugca gaaagauacg acuga                                       25

<210> SEQ ID NO 4
<211> LENGTH: 27
<212> TYPE: RNA
<213> ORGANISM: Artificial Sequence
<220> FEATURE:
<223> OTHER INFORMATION: Synthetic oligonucleotide: A1

<400> SEQUENCE: 4
ucagucguau cuuucugcag cuuccgu                                     27

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide: S1-NH2
<220> FEATURE:
<221> NAME/KEY: misc_feature
<223> OTHER INFORMATION: Modified 5'-terminus
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 5
```
ggaagcugca gaaagauacg acuga                                          25

<210> SEQ ID NO 6
<211> LENGTH: 25
<212> TYPE: RNA
<213> ORGANISM: Artificial Sequence
<220> FEATURE:
<223> OTHER INFORMATION: Synthetic oligonucleotide: S1-NH2
<220> FEATURE:
<221> NAME/KEY: misc_feature
<223> OTHER INFORMATION: Modified 5'-terminus

<400> SEQUENCE: 6
ggaagcugca gaaagauacg acuga                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide: S3-NH2
<220> FEATURE:
<221> NAME/KEY: misc_feature
<223> OTHER INFORMATION: Modified 5'-terminus
<220> FEATURE:
<221> NAME/KEY: modified_base
<222> LOCATION: (6)..(6)
<223> OTHER INFORMATION: 2'-fluoro-C
<220> FEATURE:
<221> NAME/KEY: modified_base
<222> LOCATION: (7)..(7)
<223> OTHER INFORMATION: 2'-fluoro-U
<220> FEATURE:
<221> NAME/KEY: modified_base
<222> LOCATION: (9)..(9)
<223> OTHER INFORMATION: 2'-fluoro-C
<220> FEATURE:
<221> NAME/KEY: modified_base
<222> LOCATION: (17)..(17)
<223> OTHER INFORMATION: 2'-fluoro-U
<220> FEATURE:
<221> NAME/KEY: modified_base
<222> LOCATION: (19)..(19)
<223> OTHER INFORMATION: 2'-fluoro-C
<220> FEATURE:
<221> NAME/KEY: modified_base
<222> LOCATION: (22)..(22)
<223> OTHER INFORMATION: 2'-fluoro-C
<220> FEATURE:
<221> NAME/KEY: modified_base
<222> LOCATION: (23)..(23)
<223> OTHER INFORMATION: 2'-fluoro-U
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 7
ggaagcugca gaaagauacg acuga                                          25

<210> SEQ ID NO 8
<211> LENGTH: 27
<212> TYPE: RNA
<213> ORGANISM: Artificial Sequence
<220> FEATURE:
<223> OTHER INFORMATION: Synthetic oligonucleotide: A1-NH2
<220> FEATURE:
<221> NAME/KEY: misc_feature
<223> OTHER INFORMATION: Modified 5'-terminus

<400> SEQUENCE: 8
ucagucguau cuuucugcag cuuccgu                                              27

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 9
cuuccucucu uucucuccu uguga                                                 25

<210> SEQ ID NO 10
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 10
ucacaaggga gagaaagaga ggaagga                                              27

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 11
ggaagcugca gaaagauacg acuga                                                25

<210> SEQ ID NO 12
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 12
ucagugguau cuuucugcag cuuccgu                                              27

<210> SEQ ID NO 13
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 13

```
ggaagcugca gaaagauacg acuga                                          25

<210> SEQ ID NO 14
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 14 ucaguggu au cuuucugcag cuuccgu                                        27

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: 2'-fluoro-C
<220> FEATURE:
<221> NAME/KEY: modified_base
<222> LOCATION: (7)..(7)
<223> OTHER INFORMATION: 2'-fluoro-U
<220> FEATURE:
<221> NAME/KEY: modified_base
<222> LOCATION: (9)..(9)
<223> OTHER INFORMATION: 2'-fluoro-C
<220> FEATURE:
<221> NAME/KEY: modified_base
<222> LOCATION: (17)..(17)
<223> OTHER INFORMATION: 2'-fluoro-U
<220> FEATURE:
<221> NAME/KEY: modified_base
<222> LOCATION: (19)..(19)
<223> OTHER INFORMATION: 2'-fluoro-C
<220> FEATURE:
<221> NAME/KEY: modified_base
<222> LOCATION: (22)..(22)
<223> OTHER INFORMATION: 2'-fluoro-C
<220> FEATURE:
<221> NAME/KEY: modified_base
<222> LOCATION: (23)..(23)
<223> OTHER INFORMATION: 2'-fluoro-U
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 15
ggaagcugca gaaagauacg acuga                                          25

<210> SEQ ID NO 16
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 16 ucaguggu au cuuucugcag cuuccgu                                        27

<210> SEQ ID NO 17
<211> LENGTH: 25
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: misc_feature
<223> OTHER INFORMATION: Modified 5'-terminus
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 17
ggaagcugca gaaagauacg acuga                                              25

<210> SEQ ID NO 18
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 18 ucaguggau cuuucugcag cuuccgu                                             27

<210> SEQ ID NO 19
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Modified 5'-terminus

<400> SEQUENCE: 19
ggaagcugca gaaagauacg acuga                                              25

<210> SEQ ID NO 20
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 20 ucaguggau cuuucugcag cuuccgu                                             27

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Modified 5'-terminus
<220> FEATURE:
<221> NAME/KEY: modified_base
<222> LOCATION: (6)..(6)
<223> OTHER INFORMATION: 2'-fluoro-C
<220> FEATURE:
<221> NAME/KEY: modified_base
<222> LOCATION: (7)..(7)
<223> OTHER INFORMATION: 2'-fluoro-U
<220> FEATURE:
<221> NAME/KEY: modified_base
<222> LOCATION: (9)..(9)
<223> OTHER INFORMATION: 2'-fluoro-C
```

```
<220> FEATURE:
<221> NAME/KEY: modified_base
<222> LOCATION: (17)..(17)
<223> OTHER INFORMATION: 2'-fluoro-U
<220> FEATURE:
<221> NAME/KEY: modified_base
<222> LOCATION: (19)..(19)
<223> OTHER INFORMATION: 2'-fluoro-C
<220> FEATURE:
<221> NAME/KEY: modified_base
<222> LOCATION: (22)..(22)
<223> OTHER INFORMATION: 2'-fluoro-C
<220> FEATURE:
<221> NAME/KEY: modified_base
<222> LOCATION: (23)..(23)
<223> OTHER INFORMATION: 2'-fluoro-U
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 21
ggaagcugca gaaagauacg acuga                                          25

<210> SEQ ID NO 22
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 22
ucagugguau cuuucugcag cuuccgu                                        27

<210> SEQ ID NO 23
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Modified 5'-terminus

<400> SEQUENCE: 23
ucagucguau cuuucugcag cuuccgu                                        27

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (24)..(24)
<223> OTHER INFORMATION: 2'-deoxyguanosine
<220> FEATURE:
<221> NAME/KEY: modified_base
<222> LOCATION: (25)..(25)
<223> OTHER INFORMATION: 2'-deoxyadenosine

<400> SEQUENCE: 24
ggaagcugca gaaagauacg acuga                                          25

<210> SEQ ID NO 25
<211> LENGTH: 27
```

```
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Modified 5'-terminus

<400> SEQUENCE: 25
ucagucguau cuuucugcag cuuccgu                                              27

<210> SEQ ID NO 26
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 26
ggaagcugca gaaagauacg acuga                                                25

<210> SEQ ID NO 27
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Modified 5'-terminus

<400> SEQUENCE: 27
ucagucguau cuuucugcag cuuccgu                                              27

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: 2'-fluoro-C
<220> FEATURE:
<221> NAME/KEY: modified_base
<222> LOCATION: (7)..(7)
<223> OTHER INFORMATION: 2'-fluoro-U
<220> FEATURE:
<221> NAME/KEY: modified_base
<222> LOCATION: (9)..(9)
<223> OTHER INFORMATION: 2'-fluoro-C
<220> FEATURE:
<221> NAME/KEY: modified_base
<222> LOCATION: (17)..(17)
<223> OTHER INFORMATION: 2'-fluoro-U
<220> FEATURE:
<221> NAME/KEY: modified_base
<222> LOCATION: (19)..(19)
<223> OTHER INFORMATION: 2'-fluoro-C
<220> FEATURE:
<221> NAME/KEY: modified_base
<222> LOCATION: (22)..(22)
<223> OTHER INFORMATION: 2'-fluoro-C
<220> FEATURE:
<221> NAME/KEY: modified_base
<222> LOCATION: (23)..(23)
<223> OTHER INFORMATION: 2'-fluoro-U
<220> FEATURE:
<221> NAME/KEY: modified_base
<222> LOCATION: (24)..(24)
<223> OTHER INFORMATION: 2'-deoxyguanosine
<220> FEATURE:
```

```
<221> NAME/KEY: modified_base
<222> LOCATION: (25)..(25)
<223> OTHER INFORMATION: 2'-deoxyadenosine

<400> SEQUENCE: 28
ggaagcugca gaaagauacg acuga                                              25
```